(12) United States Patent
Pilgeram et al.

(10) Patent No.: US 10,722,343 B2
(45) Date of Patent: Jul. 28, 2020

(54) FIXATION MEMBER WITH SEPARATE EYELET AND METHODS OF USE THEREOF

(71) Applicant: Stryker Corporation, Kalamazoo, MI (US)

(72) Inventors: Kyle Craig Pilgeram, San Jose, CA (US); Mark Larson, Lone Tree, CO (US)

(73) Assignee: Stryker Corporation, Kalamazoo, MI (US)

( * ) Notice: Subject to any disclaimer, the term of this patent is extended or adjusted under 35 U.S.C. 154(b) by 142 days.

(21) Appl. No.: 15/901,008

(22) Filed: Feb. 21, 2018

(65) Prior Publication Data

US 2018/0235746 A1    Aug. 23, 2018

Related U.S. Application Data

(60) Provisional application No. 62/522,372, filed on Jun. 20, 2017, provisional application No. 62/462,153, filed on Feb. 22, 2017.

(51) Int. Cl.
*A61B 17/04* (2006.01)
*A61F 2/08* (2006.01)
*A61F 2/30* (2006.01)

(52) U.S. Cl.
CPC ........ *A61F 2/0811* (2013.01); *A61B 17/0401* (2013.01); *A61B 17/0483* (2013.01);
(Continued)

(58) Field of Classification Search
CPC ............ A61B 17/0401; A61B 17/1615; A61B 17/1671; A61B 17/1604; A61B 17/1659; A61B 17/7074; A61B 17/863; A61B 17/8811; A61B 10/0233; A61B 17/00234; A61B 17/0206; A61B 17/0482; A61B 17/06166; A61B 17/062; A61B 17/0642; A61B 17/17; A61B 17/1735; A61B 17/56; A61B 17/68; A61B 2017/0409;
(Continued)

(56) References Cited

U.S. PATENT DOCUMENTS 4,738,255 A    4/1988    Goble et al.
4,772,286 A    9/1988    Goble et al.
(Continued)

OTHER PUBLICATIONS

Partial European Search Report for European Application No. 18158041 dated Aug. 7, 2018.

*Primary Examiner* — Ann Schillinger
(74) *Attorney, Agent, or Firm* — Lerner, David, Littenberg, Krumholz & Mentlik, LLP

(57) ABSTRACT

In one embodiment of the present disclosure, an implant system for securing tissue to bone, including a first fixation member releasably engaged to a first inserter, the first fixation member having a throughbore adapted to accept a filament therethrough and a cannulation extending from a proximal end of the first fixation member to a distal end of the first fixation member, the first inserter positioned through the cannulation and having a distal tip extending distally beyond the distal end of the first fixation member, and a second fixation member releasably engaged to a second inserter different from the first inserter, the second fixation member having a size capable of being positioned within the bonehole.

20 Claims, 24 Drawing Sheets

(52) U.S. Cl.
CPC ..... *A61B 17/0485* (2013.01); *A61B 2017/044* (2013.01); *A61B 2017/0409* (2013.01); *A61B 2017/0412* (2013.01); *A61B 2017/0414* (2013.01); *A61B 2017/0416* (2013.01); *A61B 2017/0424* (2013.01); *A61B 2017/0425* (2013.01); *A61B 2017/0427* (2013.01); *A61B 2017/0445* (2013.01); *A61F 2002/0835* (2013.01); *A61F 2002/0841* (2013.01); *A61F 2002/0852* (2013.01); *A61F 2002/0888* (2013.01); *A61F 2002/3085* (2013.01); *A61F 2220/0016* (2013.01)

(58) Field of Classification Search
CPC .... A61B 2017/0414; A61B 2017/0427; A61B 2017/0445; A61B 2017/0496; A61B 2017/06171; A61B 2017/06185; A61B 2017/22038; A61B 2017/22061; A61B 2017/2215; A61B 2017/2937; A61B 2017/320082; A61F 2/0811; A61F 2/4611; A61F 2002/30387; A61F 2002/0072; A61F 2002/0817; A61F 2002/0852; A61F 2002/0858; A61F 2002/0888; A61F 2002/285; A61F 2002/30579; A61F 2002/30904; A61F 2220/0008; A61F 2220/0016
See application file for complete search history.

(56) References Cited

U.S. PATENT DOCUMENTS

| | | |
|---|---|---|
| 5,176,682 A | 1/1993 | Chow |
| 5,208,001 A | 5/1993 | Truitt et al. |
| 5,312,438 A | 5/1994 | Johnson |
| 5,324,308 A | 6/1994 | Pierce |
| 5,464,427 A | 11/1995 | Curtis et al. |
| 5,470,334 A | 11/1995 | Ross et al. |
| 5,472,452 A | 12/1995 | Trott |
| 5,480,403 A | 1/1996 | Lee et al. |
| 5,486,197 A | 1/1996 | Le et al. |
| 5,501,695 A | 3/1996 | Anspach, Jr. et al. |
| 5,569,306 A | 10/1996 | Thal |
| 5,632,748 A | 5/1997 | Beck, Jr. et al. |
| 5,643,321 A | 7/1997 | McDevitt |
| 5,649,963 A | 7/1997 | McDevitt |
| 5,688,285 A | 11/1997 | Yamada |
| 5,702,398 A | 12/1997 | Tarabishy |
| 5,707,395 A | 1/1998 | Li |
| 5,720,753 A | 2/1998 | Sander et al. |
| 5,742,452 A | 4/1998 | Simmons et al. |
| 5,785,713 A | 7/1998 | Jobe |
| 5,797,963 A | 8/1998 | McDevitt |
| 5,859,938 A | 1/1999 | Nabeyama et al. |
| 5,899,938 A | 5/1999 | Sklar et al. |
| 5,911,721 A | 6/1999 | Nicholson et al. |
| 5,928,244 A | 7/1999 | Tovey et al. |
| 5,957,953 A | 9/1999 | DiPoto et al. |
| 5,968,078 A | 10/1999 | Grotz |
| 6,022,373 A | 2/2000 | Li |
| 6,128,711 A | 10/2000 | Duncan et al. |
| 6,267,766 B1 | 7/2001 | Burkhart |
| 6,290,711 B1 | 9/2001 | Caspari et al. |
| 6,319,252 B1 | 11/2001 | McDevitt et al. |
| 6,527,794 B1 | 3/2003 | McDevitt et al. |
| 6,544,281 B2 | 4/2003 | ElAttrache et al. |
| 6,562,071 B2 | 5/2003 | Jarvinen |
| 6,585,730 B1 | 7/2003 | Foerster |
| 6,641,596 B1 | 11/2003 | Lizardi |
| 6,652,560 B1 | 11/2003 | Gerke et al. |
| 6,660,023 B2 | 12/2003 | McDevitt et al. |
| 6,692,516 B2 | 2/2004 | West, Jr. et al. |
| 6,887,271 B2 | 5/2005 | Justin et al. |
| 7,008,451 B2 | 3/2006 | Justin et al. |
| 7,037,324 B2 | 5/2006 | Martinek |
| 7,235,100 B2 | 6/2007 | Martinek |
| 7,324,272 B1 | 1/2008 | Deck |
| 7,329,272 B2 | 2/2008 | Burkhart et al. |
| 7,381,213 B2 | 6/2008 | Lizardi |
| 7,517,357 B2 | 4/2009 | Abrams et al. |
| 7,572,283 B1 | 8/2009 | Meridew |
| 7,585,311 B2 | 9/2009 | Green et al. |
| 7,651,528 B2 | 1/2010 | Montgomery et al. |
| 7,662,171 B2 | 2/2010 | West, Jr. et al. |
| 7,713,285 B1 | 5/2010 | Stone et al. |
| 7,803,173 B2 | 9/2010 | Burkhart et al. |
| 7,828,820 B2 | 11/2010 | Stone et al. |
| 7,979,565 B2 | 7/2011 | Leitheiser et al. |
| 7,981,140 B2 | 7/2011 | Burkhart |
| 7,993,369 B2 | 8/2011 | Dreyfuss |
| 8,012,174 B2 | 9/2011 | ElAttrache et al. |
| 8,057,524 B2 | 11/2011 | Meridew |
| 8,062,295 B2 | 11/2011 | McDevitt et al. |
| 8,100,942 B1 | 1/2012 | Green et al. |
| 8,109,969 B1 | 2/2012 | Green et al. |
| 8,114,127 B2 | 2/2012 | West, Jr. |
| 8,419,794 B2 | 4/2013 | ElAttrache et al. |
| 8,430,909 B2 | 4/2013 | Dreyfuss |
| 8,465,522 B2 | 6/2013 | Burkhart |
| 8,506,596 B2 | 8/2013 | Stone et al. |
| 8,512,405 B2 | 8/2013 | Baird |
| 8,518,091 B2 | 8/2013 | McDevitt et al. |
| 8,529,610 B2 | 9/2013 | Graf et al. |
| 8,663,279 B2 | 3/2014 | Burkhart et al. |
| 8,771,351 B2 | 7/2014 | ElAttrache et al. |
| 8,845,685 B2 | 9/2014 | Stone et al. |
| 8,951,287 B1 | 2/2015 | Green et al. |
| 9,005,246 B2 | 4/2015 | Burkhart et al. |
| 9,179,907 B2 | 11/2015 | ElAttrache et al. |
| 9,226,817 B2 | 1/2016 | Dougherty et al. |
| 9,241,703 B2 | 1/2016 | Lanois et al. |
| 9,241,705 B2 | 1/2016 | Lanois et al. |
| 9,247,933 B2 | 2/2016 | Lanois et al. |
| 9,259,307 B2 | 2/2016 | Graf et al. |
| 9,271,717 B2 | 3/2016 | Lanois et al. |
| 9,408,690 B2 | 8/2016 | Graf et al. |
| 9,566,060 B2 | 2/2017 | Dougherty et al. |
| 9,706,986 B2 | 7/2017 | ElAttrache et al. |
| 9,717,587 B2 | 8/2017 | Dougherty et al. |
| 9,770,240 B2 | 9/2017 | Dougherty et al. |
| 9,775,599 B2 | 10/2017 | ElAttrache et al. |
| 9,782,250 B2 | 10/2017 | Dougherty et al. |
| 9,795,374 B2 | 10/2017 | Dougherty et al. |
| 2002/0032345 A1 | 3/2002 | Kajihara et al. |
| 2004/0193217 A1 | 9/2004 | Lubbers et al. |
| 2006/0235413 A1 | 10/2006 | Denham et al. |
| 2008/0281325 A1 | 11/2008 | Stone et al. |
| 2009/0287259 A1 | 11/2009 | Trenhaile et al. |
| 2012/0150226 A1 | 6/2012 | Burkhart et al. |
| 2013/0035721 A1* | 2/2013 | Brunelle ............ A61B 17/0401 606/232 |
| 2013/0150885 A1 | 6/2013 | Dreyfuss |
| 2014/0277134 A1 | 9/2014 | ElAttrache et al. |
| 2017/0150960 A1 | 6/2017 | Dougherty et al. |
| 2017/0303912 A1 | 10/2017 | ElAttrache et al. |

* cited by examiner

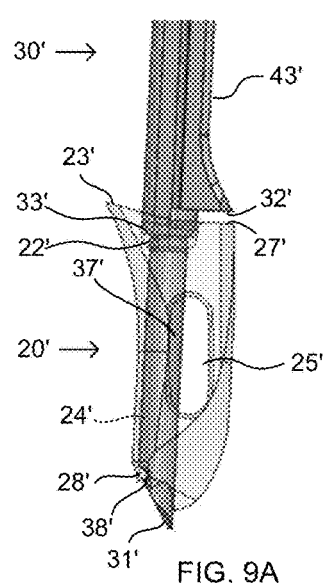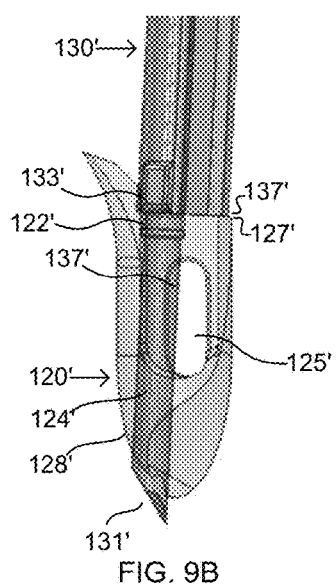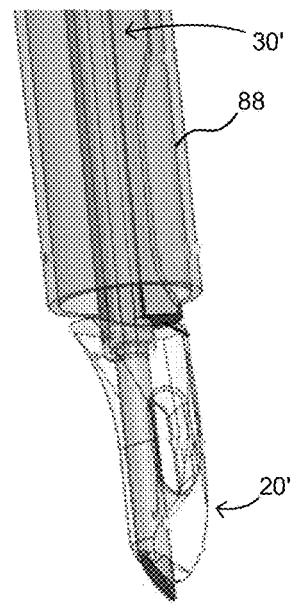
FIG. 9A  FIG. 9B  FIG. 9C
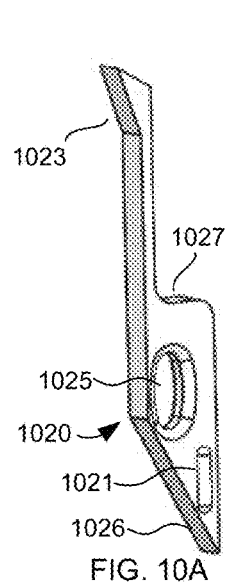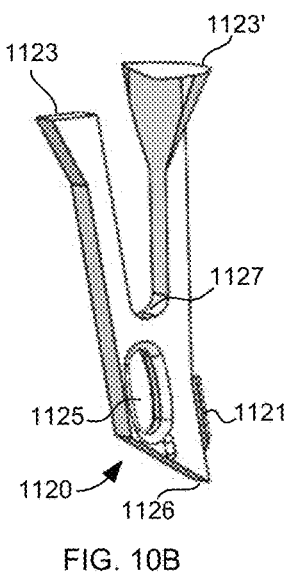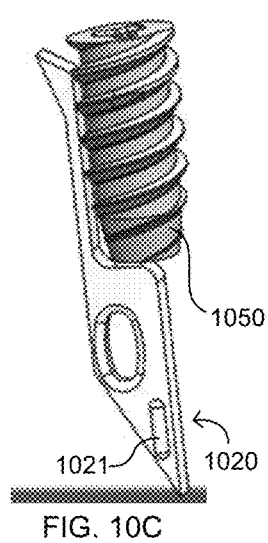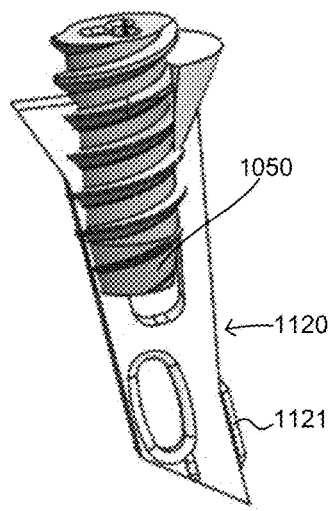
FIG. 10A  FIG. 10B  FIG. 10C  FIG. 10D

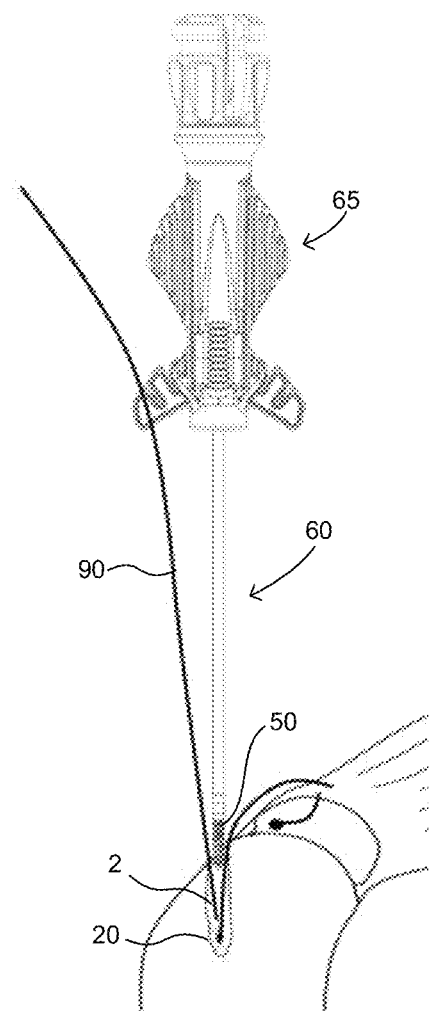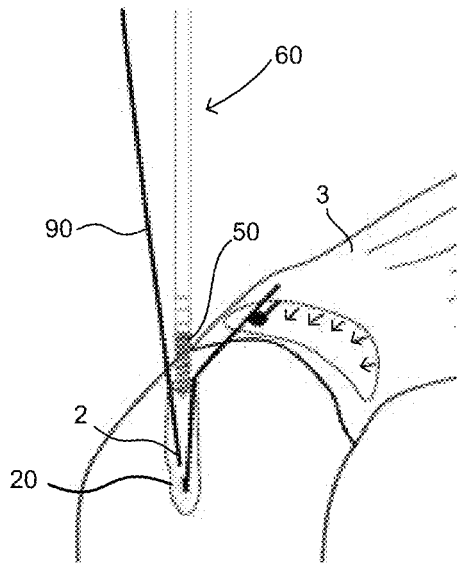
FIG. 16C
FIG. 16D

FIXATION MEMBER WITH SEPARATE EYELET AND METHODS OF USE THEREOF

CROSS-REFERENCE TO RELATED APPLICATIONS

This application claims the benefit of the filing date of U.S. Provisional Patent Application No. 62/522,372 filed on Jun. 20, 2017, and U.S. Provisional Patent Application No. 62/462,153 filed on Feb. 22, 2017, the disclosures of which are hereby incorporated herein by reference as if fully set forth herein.

BACKGROUND OF THE INVENTION

There are many medical procedures where a surgeon needs to attach soft tissue to bone. The soft tissue can be tendon or other connective tissue. One very common example of this is rotator cuff repair where a portion or all of the rotator cuff is torn or detached from the humerus. When the rotator cuff tears from the humerus, the result is pain and loss of function. When a patient presents with a significant rotator cuff tear, surgical repair is performed. The goal of surgical repair of the rotator cuff is to secure the tendon to the bone in a stabile manner so that the tendon can reattach to the bone and can heal. If the tendon is not stable and oscillation or micro-motion between the tendon and bone develops, the healing process will be interrupted. In this situation, it is less likely that the tendon will heal properly to the bone, resulting in a re-tear. Thus, the more stable the repair, the more successfully the tendon will heal to the bone.

Arthroscopic rotator cuff repair has grown in popularity in recent years, and more specifically, the use of "knotless" suture anchors has also become the technique of choice for many surgeons and other operators. However, current knotless suture anchors may be overly complex to use or do not provide for adequate tension to the suture, resulting in the aforementioned instability of the repair resulting in micro-motion of the tissue. Current knotless suture anchors also lack a reliable "self-tapping" technique, whereby the anchor can be implanted into bone without the need of a bonehole created prior to implantation.

Thus, there is a need in the art for a reliable, reproducible knotless suture anchor and methodology that can obtain consistently strong results while being simple to use.

BRIEF SUMMARY OF THE INVENTION

The present disclosure generally relates to implants for securing tissue, such as native tissue, a graft, or the like, in a patient. Specifically, the implant can secure a length of filament used to secure tissue to other tissue, such as bone. In one embodiment, the filament can be secured without tying any knots.

In one embodiment, the present disclosure includes an implant system for securing tissue to bone, including a first fixation member releasably engaged to a first inserter, the first fixation member having a throughbore adapted to accept a filament therethrough and a cannulation extending from a proximal end of the first fixation member to a distal end of the first fixation member, the first inserter positioned through the cannulation and having a distal tip extending distally beyond the distal end of the first fixation member; and a second fixation member releasably engaged to a second inserter different from the first inserter, the second fixation member having a size capable of being positioned within the bonehole. Further, the distal tip may be adapted to initiate a bonehole in the bone. Additionally, the first fixation member includes at least one tissue engaging feature adapted to engage bone material adjacent the bonehole, such as a barb extending laterally from the proximal end in a first lateral direction relative to a longitudinal direction of the first fixation member and first inserter. The first fixation member can also include a deformable portion and the first inserter includes a groove matingly received by the deformable portion, wherein the deformable portion is deformable between a mating position and a release position.

In another embodiment, the present disclosure includes an implant system for securing tissue to bone, including an eyelet releasably engaged to a first inserter, the eyelet having a throughbore adapted to accept a filament therethrough, a barb extending laterally from the proximal end in a first lateral direction relative to a longitudinal direction of the eyelet and first inserter, a deformable portion deformable between a mating position and a release position, and a cannulation extending from a proximal end of the eyelet to a distal end of the eyelet; and the first inserter positioned through the cannulation and having a distal tip extending distally beyond the distal end of the eyelet, the distal tip adapted to initiate a bonehole in the bone, a groove matingly received by the deformable portion when in the mating position, and a shaft extending proximally from the distal tip, through the cannulation of the eyelet, and to a handle, and a first pocket having a distal surface tapering in the first lateral direction, a proximal surface tapering in a second lateral direction opposite the first lateral direction, and a flat surface in between the proximal and distal tapering surfaces, wherein at least a portion of the pocket coincides, in a longitudinal direction along the shaft, with the barb of the eyelet. The system may further include a fixation member releasably engaged to a second inserter different from the first inserter, the fixation member having a size capable of being positioned within the bonehole. Additionally, the first inserter can also include a shoulder positioned adjacent the proximal end of the eyelet, the shoulder separated from the proximal end when the deformable portion is in the mating position with the groove and the shoulder abutting the proximal end when the deformable portion is in the release position.

In a further embodiment, the present disclosure includes an implant system for securing tissue to bone including an eyelet releasably engaged to a first inserter, the eyelet having a throughbore adapted to accept a filament therethrough, a cannulation extending from a proximal end of the eyelet to a distal end of the eyelet, and a deformable portion positioned in communication with the cannulation and deformable between a mating position and a release position; and the first inserter positioned through the cannulation and having a distal tip extending distally beyond the distal end of the eyelet, the distal tip adapted to initiate a bonehole in the bone, a groove matingly received by the deformable portion when in the mating position, a shoulder positioned adjacent the proximal end of the eyelet, the shoulder separated from the proximal end when the deformable portion is in the mating position with the groove and the shoulder abutting the proximal end when the deformable portion is in the release position, and a shaft extending proximally from the distal tip, through the cannulation of the eyelet, and to a handle. The eyelet may also include a barb extending laterally from the proximal end in a first lateral direction relative to a longitudinal direction of the eyelet and first inserter. The first inserter may also include a first pocket having a distal surface tapering in the first lateral direction, a proximal surface tapering in a second lateral direction opposite the first lateral direction, and a flat surface in between the proximal and distal tapering surfaces oriented in the longitudinal direction, wherein at least a portion of the pocket coincides, in a longitudinal direction along the shaft, with the barb of the eyelet.

In yet another embodiment, the present disclosure includes an implant system for securing tissue to bone, including a first fixation member, a second fixation member, and an inserter with both the first and second fixation members positioned thereon. Further, the system may be self-tapping, and further, the inserter may include a distal tip adapted to be self-tapping. Additionally, both the first and second fixation members may be formed of PEEK. Still further, the PEEK first and second fixation members may be cannulated such that the self-tapping distal tip of the inserter can extend distally of both fixation members. Furthermore, the first fixation member may be positioned adjacent and proximal to the distal tip of the inserter, and the second fixation member may be positioned proximal to the first fixation member. The second fixation member may be spaced apart from the first fixation member on the inserter, such that during insertion, with the first fixation member and the distal tip positioned in bone, the second fixation member is moved distally into direct contact with the first fixation member within the bone.

In still a further embodiment, the present disclosure includes a method of repairing tissue including the steps of: obtaining an implant system including a first fixation member formed of PEEK, a second fixation member formed of PEEK, and an inserter with both the first and second fixation members positioned thereon and having a distal tip; inserting the distal tip into a bone to position the first fixation member in bone; and actuating the second fixation member to move distally towards the first fixation member and into the bone. The inserter may be self-tapping, such that the inserting step occurs without the need for pre-drilling a hole in bone and/or otherwise preparing the bone. The first fixation member may include at least one filament engaged therewith, wherein the actuating step fixedly secures the filament relative to the bone.

In yet another embodiment, the present disclosure includes a method of securing tissue to bone, including the steps of obtaining a first inserter, the first inserter including a first fixation member releasably engaged thereon, the first fixation member including a throughbore and having at least one filament positioned through the throughbore; positioning the first fixation member and at least a portion of the first inserter into the bone; withdrawing the first inserter from the bone and from the first fixation member, the first fixation member remaining at least partially within the bone; and inserting a second fixation member, using a second inserter different from the first inserter, into the bone to secure the filament to the bone. The step of positioning may further include initiating a bonehole with a distal tip of the first inserter. In other words, the step of positioning may be performed without the need of preparing a bonehole or otherwise preparing the bone beforehand. The inserting step may also secure the first fixation member to the bone. This method may also include the step of, after withdrawing the first inserter, tensioning the filament to change the orientation of the first fixation member relative to the bone. The positioning step can further include forming a bonehole in the bone by inserting the first fixation member and at least a portion of the first inserter into the bone, where the first inserter includes a self-tapping distal tip. Further, upon inserting the second fixation member, the first fixation member may be positioned laterally relative to the second fixation member and a longitudinal axis of the bonehole. Still further, the first fixation member can include a deformable portion deformable between a mating position and a release position relative to a groove on the first inserter, wherein the deformable portion is deformed from the mating position to the release position during the positioning step. Further, the positioning step may include applying a distal driving force to the first inserter to deform the deformable portion from the mating position to the release position.

Continuing with this embodiment, the first fixation member may include a tissue engaging feature, such as a barb extending laterally from a proximal end in a first lateral direction relative to a longitudinal direction of the first fixation member and first inserter, and the first inserter may include a shaft extending proximally from a distal tip of the first inserter, through the cannulation of the first fixation member, and to a handle, and a first pocket having a distal surface tapering in the first lateral direction, a proximal surface tapering in a second lateral direction opposite the first lateral direction, and a flat surface in between the proximal and distal tapering surfaces oriented in the longitudinal direction, wherein at least a portion of the pocket coincides, in the longitudinal direction, with the barb of the first fixation member, wherein during formation of the bonehole with the self-tapping distal tip of the first inserter, the method can include moving the first fixation member into the bonehole along a longitudinal axis of the bonehole and first inserter as the first fixation member passes through the cortical layer, along a path lateral to the longitudinal axis as the barb and pocket pass through the cortical layer, and along the longitudinal axis as the shaft, proximal to the pocket, passes through the cortical layer such that the barb is positioned at least partially to the lateral side of the bonehole and in contact with bone of an inner wall of the bonehole. Further, the tensioning step may include engaging the barb with the inner wall of the bonehole to change the orientation of the first fixation member.

In one embodiment, the present disclosure includes an implant system for securing tissue to bone, including a first fixation member, adapted to be inserted into a bonehole, including a throughhole and at least one tissue engaging feature, and a second fixation member, adapted to be inserted into the bonehole after the first fixation member, including tissue engaging features. The first fixation member may also include a transverse passage in communication with the throughhole. The tissue engaging features of the first and second members may include projections, such as barbs, threads or the like, for engaging bone surrounding the bonehole.

In a further embodiment, the present disclosure includes an implant system for securing tissue to bone, including a fixation member including engaging features and a central cannulation, an eyelet including a throughhole, an inserter including an elongated shaft, a proximal handle, and a distal implant-retaining structure for retaining at least one of the fixation member and the eyelet, and a length of suture. The eyelet may also include a cleat area. The inserter may retain only one of the fixation member and the eyelet, and the system may further include a second inserter including an elongated shaft, a proximal handle, and a distal implant-retaining structure for retaining the other of the fixation member and the eyelet. The first inserter and the second inserter may be adapted for subsequent use, wherein the first inserter inserts the eyelet in the bone and the second inserter inserts the fixation member in the bone. Further, the eyelet and the fixation member may be inserted into the same bonehole in the bone.

In another embodiment, the present disclosure includes an implant system for securing tissue to bone, including a fixation member including an outer thread and a central cannulation; an eyelet including a throughhole, a cleat area, and a blocking feature temporarily in the cleat area or inhibiting access to the cleat area; an inserter including an elongated shaft, a central cannulation extending at least partially through the shaft, a proximal handle, and a distal implant engagement structure for engaging at least one of the fixation member and the eyelet; and a length of suture.

In yet another embodiment, the present disclosure includes an implant system for securing tissue to bone, including a first fixation member, adapted to be inserted into a bonehole in a bone, including an eyelet having a throughhole and at least one bone engaging feature, a second fixation member, adapted to be inserted into the bonehole after the first fixation member, including engaging features, and a length of suture passing through the throughhole of the first fixation member, wherein at least one of a) tension on the throughhole by the length of suture and b) the at least one bone engaging feature, causes the first fixation member to flip within the bone. The system may further include a first inserter adapted for insertion of the first fixation member and a second inserter, separate from the first inserter, adapted for insertion of the second fixation member.

In still another embodiment, the present disclosure includes a method of securing tissue to bone, including the steps of: inserting a first fixation member into a bonehole formed in bone, the first fixation member including a throughole and at least one bone engaging feature, subsequently, inserting a second fixation member into the bonehole, the second fixation member including engaging features. The step of inserting the first fixation member can include inserting the first fixation member with a first inserter, and the step of inserting the second fixation member can include inserting the second fixation member with a second inserter different from the first inserter. The method may further include engaging a filament, such as suture, with the first fixation member, wherein the step of inserting the first fixation member further includes inserting the filament into the bone hole with the first fixation member. The method may further include the step of, after inserting the first fixation member, applying tension to the filament to change the orientation of the first fixation member from an insertion orientation to an implanted orientation.

In yet another embodiment, the present disclosure includes a system for the repair of soft tissue including at least one fixation member, at least one inserter, and a surgical procedure. The surgical procedure may include instructions or protocol for using the fixation member(s) and inserter(s).

In an associated embodiment, the present invention includes a method of providing instructions or information to practice any of the various methods described herein. For example, the method may include supplying a surgical protocol, or like document, to provide step-by-step instructions for performing any of the method embodiments of the present invention.

BRIEF DESCRIPTION OF THE DRAWINGS

FIGS. 9A-9C illustrate additional aspects of the first fixation member and first inserter of FIGS. 2D-2E.

FIGS. 10A-10D and 11A-11C illustrate various embodiments of first fixation members and/or first inserters.

FIGS. 16A-16I illustrate various embodiments of methods of using the fixation members and inserters of the present disclosure, in particular, first fixation member, first inserter, second fixation member and second inserter of FIGS. 1A-1G, 2A-2C, 3, 4A-4F, 5A-5E and 8.

DETAILED DESCRIPTION

Figure 1A:
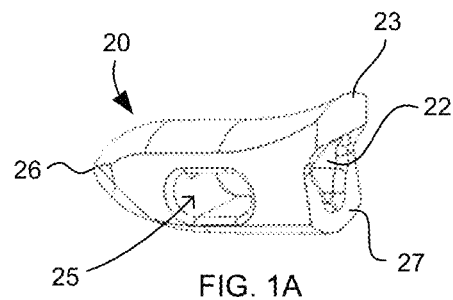
FIGS. 1A-1G illustrate one embodiment of a first fixation member of the present disclosure, in particular an eyelet.

The implants, eyelets, fixation members, and instrumentation, and associated systems, kits, and methods, of the present disclosure are intended for use in tissue, such as bone or soft tissue. Soft tissue may be, for example, meniscus, cartilage, ligaments and tendons, or the like, or artificial or natural grafts of any such tissues. As used herein, "tissue" will refer to soft tissue and "bone" will refer to bone, unless otherwise specified. While many of the exemplary methods disclosed herein are directed towards the use of the implants, eyelets and fixation members as a suture anchor for implantation into a bone hole, other uses, some of which are described herein, are also envisioned. Throughout the present application, the method of the repair of a rotator cuff in a shoulder of a patient is illustrated. This illustrated method is exemplary in nature and serves to illustrate one such use of the various implants, instrumentation, systems and kits. Others methods of surgery and other anatomical locations throughout the patient are also envisioned, such as other shoulder anatomy, hip, knee, small joints such as the ankle or in the hand or foot, and the like. As used herein, "proximal" or "proximally" means closer to or towards an operator, e.g., surgeon, while "distal" or "distally" means further from or away from the operator.

As used herein, the term "filament" and like terms are inclusive of single or multiple strands, threads, fibers, tapes, strings, wires or sutures in which such terms preferably refer to a suture or other thread-like material, and in particular a braided suture, having a hollow core along at least a portion of its length. A filament may be constructed from homogenous or heterogeneous materials such as, but not limited to, polyester, polyethylene (including ultra-high molecular weight polyethylene (UHMWPE)), polytetrafluoroethylene (including expanded polytetrafluorethylene), nylon, polypropylene, aramids (such as Kevlar-based materials), polydioxanone, polygycolic acid or other absorbable material, liquid crystal polymer (LCP), organic material (silk, animal tendon, or the like), metallic wire, or any combination of these materials. For example, the suture could constitute two portions of a suture that is passed through tissue or graft material whereby the two portions, or end portions, are brought to the implant. Alternatively, the filament could constitute multiple lengths of separate sutures which together are engaged by the implant.

The implants of the present disclosure include, in some embodiments, a fixation member and an eyelet. The eyelet can be integrated or otherwise connected to the fixation member. Alternatively, the eyelet can be separate from the fixation member, and would typically be engaged with a filament and implanted first into bone, followed by the fixation member to finalize the implantation and securement of the filament to the bone. The fixation member can be, for example, a screw or plug which can secure a filament in a bonehole via an interference fit between the screw or plug and the wall of the bone hole. The fixation member and eyelet may be formed of any material, such as any biocompatible materials including polymers (PEEK, biodegradable materials, etc.), metals (stainless steel, titanium), ceramics, tissue-based materials (allografts, autografts, artificial tissue grafts, etc.), or the like, or any combinations of such materials. For example, the fixation member and eyelet may both be formed entirely of PEEK, which is the material used for the various exemplary embodiments herein.

An exemplary embodiment of an implant system of the present disclosure is illustrated in FIGS. 1A-2C, 3-6A, 7A and 8. As illustrated, the resulting implant system includes a first fixation member, such as eyelet 20, and a second fixation member, such as fixation member 50. The eyelet, being separate from the fixation member, is positioned on a first inserter, such as an awl 30, while the fixation member 50 is positioned on a second inserter, which is different from the first inserter, such as inserter 60. As such, eyelet 20 and fixation member 50 each have a dedicated inserter. As discussed further below, positioning the eyelet 20 on the awl 30 may provide for both formation of a bonehole in bone and implantation of the eyelet into the bone in a single step. The eyelet 20 may be positioned in the bone first, with a filament passed through a throughbore 25, such that eyelet 20 sits below the surface of the bone, preferably in the cancellous below the cortical layer, to maintain the filament within the bone. After removal of the awl 30 from the bonehole, and with the eyelet 20 remaining within the bone (e.g., at least partially within the bonehole and, optionally, partially within the cancellous forming the inner wall of the bonehole) with the filament, fixation member 50 may then be implanted into the bonehole to secure the filament and eyelet to the bone. In other words, the repair is complete with the eyelet 20 and fixation member 50 together establishing a fixed securement of the filament to the bone.

With reference to FIGS. 1A-G, eyelet 20 includes a distal end 26 and a proximal end 27, throughbore 25, a cannulation 24 along a longitudinal direction of the eyelet 20 between a distal opening 21 and a proximal opening 22, and a tissue engaging feature suitable for engaging tissue (e.g., bone around the formed bonehole), such as a barb 23. Barb 23 extends laterally from the proximal end 27 in a first lateral direction.

Figure 1B:
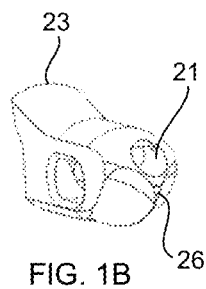
Figure 1C:
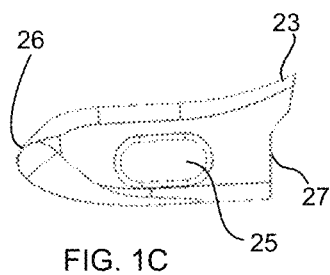
Figure 1D:
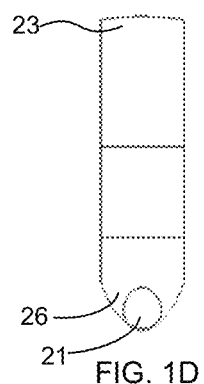
Figure 1E:
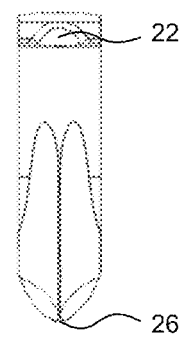
Figure 1F:
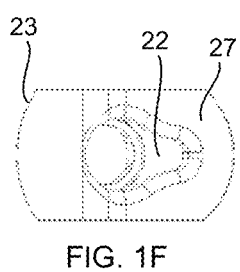
Figure 1G:
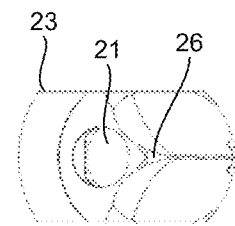
Figure 2A:
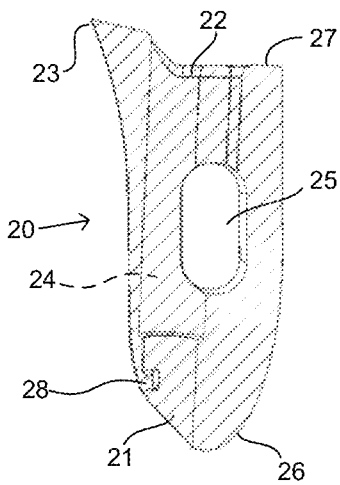
FIGS. 2A-2C illustrate the first fixation member of FIGS. 1A-1G in cross-section and/or in combination with one embodiment of a first inserter of the present disclosure, in particular an awl.
Figure 2B:
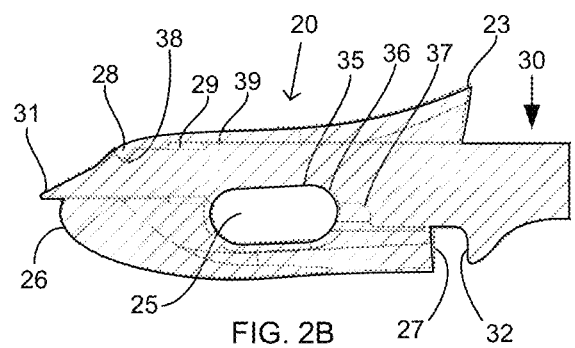

The cannulation 24 of eyelet 20 is shaped to accept a portion of the first inserter, such as awl 30, therethrough. As illustrated in FIGS. 2A-B, awl 30 is positioned such that a distal tip 31 extends distally beyond the distal end 26 of eyelet 20. The distal tip 31 may have a sharp tip suitable for initiating the formation of the bonehole in bone. Further, the eyelet 20 is shaped such that it can work in conjunction with the distal tip 31 to form the bonehole. For example, as illustrated in FIGS. 1B and 1G, the distal end 26 of eyelet 20 may taper to an edge such that the edge can facilitate formation of the bonehole. In other words, the distal tip 31, together with distal end 26, combine to form a distal surface adapted to form the bonehole. Cannulation 24 and the distal portion of awl 30 may be noncircular such that the relative orientation of the awl and eyelet remains the same and the eyelet cannot rotate relative to the awl. Notch 37, and other such structures on the awl 30 can further assist in maintaining orientation and alignment of the eyelet and the awl, particularly during impaction of the awl and eyelet into the bone. Additionally, as discussed further below, positioning the awl through cannulation 24 of the eyelet may also improve overall system strength to allow for impaction of the awl and eyelet into the bone using a mallet or the like.

Figure 2C:
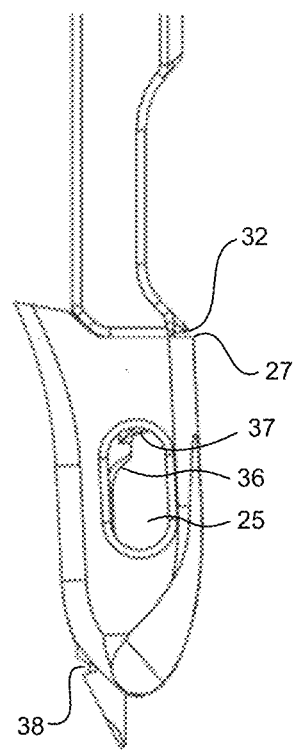

The distal portion of the first inserter of this embodiment, awl 30, also includes a shoulder 32 which, with eyelet 20 positioned on the awl 30, is adjacent the proximal end 27 but spaced from one another, as illustrated in FIG. 2B. As discussed below, this spacing between proximal end 27 and shoulder 32 allows for a specified range of relative motion between awl 30 and eyelet 20, for example upon application of a force to the awl and eyelet to transition the relationship as illustrated in FIG. 2C, as explained below. In the example of FIG. 2E, the specified range is a gap of about 0.015". Additional shoulder 39 is spaced from stop 29 on eyelet 20 which provides an additional corresponding structure between the eyelet and awl which may provide a further abutment or stop feature, and/or may provide additional strength to the overall structure of the eyelet and awl system. Awl 30 also includes cutout 35, which limits the interference of throughbore 25 by awl 30. Awl 30 also includes a tapered surface 36 and a notch 37, both of which are shaped to minimize interaction with throughbore 25 while still providing additional strength and stability to the awl and eyelet system, particularly during implantation of the eyelet and preparation of the bonehole, and to resist relative rotational movement between the awl and eyelet.

The eyelet 20 also includes a mating structure which may releasably attach the eyelet to the awl 30. In this embodiment, as illustrated in FIGS. 2A-B, this mating structure has a deformable portion 28, which is positioned such that it can have a mating relationship with awl 30, which as illustrated, includes a groove 38. Deformable portion 28 is deformable between a mating position, where it is positioned within groove 38 (FIGS. 2A-B) and has a first staying force to maintain the eyelet on the awl, and a release position, where it is deformed (FIG. 2C) such that it has a second staying force that is less than the first staying force. As such, the eyelet 20 is attached to awl 30 when deformable portion 28 is in the mating position, and eyelet 20 can be released from awl 30 when the deformable portion is in the release position. For example, deformable portion, in the mating position, may impart sufficient holding force such that at least about 4 pounds, preferably about 4 pounds to about 8 pounds of force, and more preferably at least about 5 pounds to about 8 pounds, is required to remove the eyelet from the awl, while in the release position, only about 2 pounds or less of force, preferably about 1.5 pounds or less, is required to remove the eyelet from the awl. Optionally, a slap hammer or the like may be used to remove the awl, in instances where the deformable portion 28 did not deform, the bone is particularly tight around the awl, etc.

Figure 3:
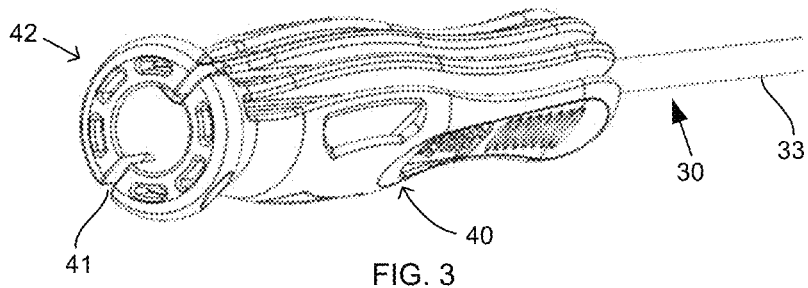
FIG. 3 illustrates further aspects of the first inserter of FIGS. 2A-2C.
Figure 4A:
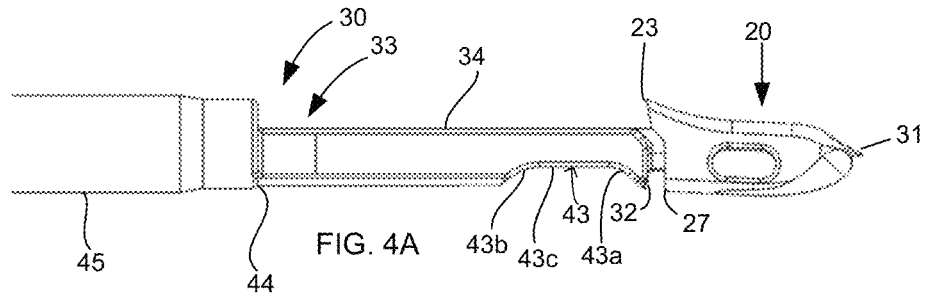
FIGS. 4A-4F illustrate still further aspects of the first inserter and first fixation member of FIGS. 1A-1G, 2A-2C, and 3.
Figure 4B:
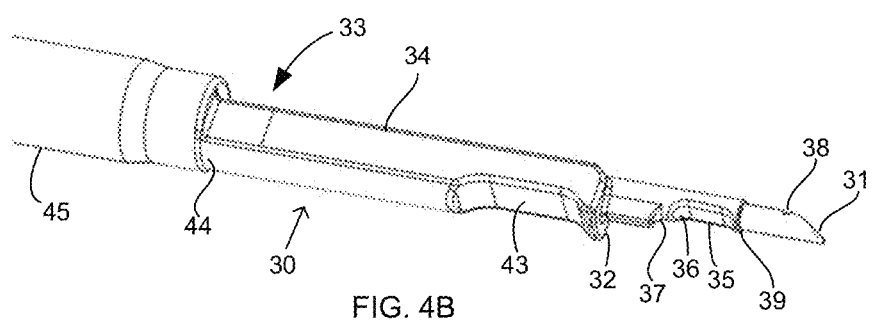
Figure 4C:
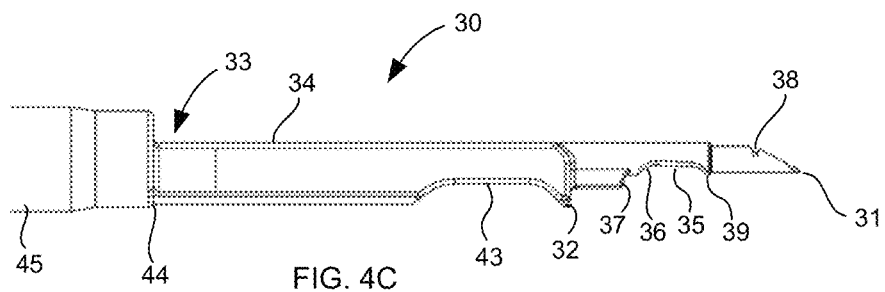
Figure 4D:
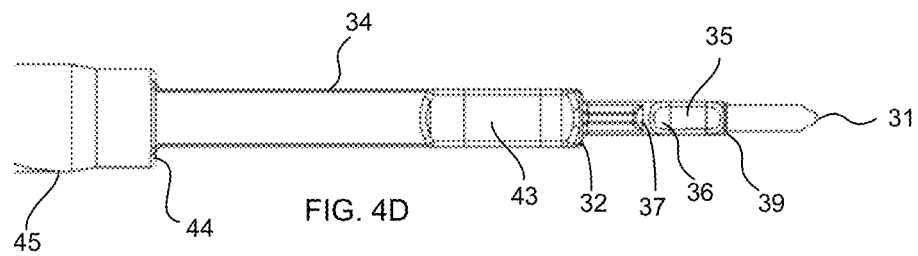
Figure 4E:
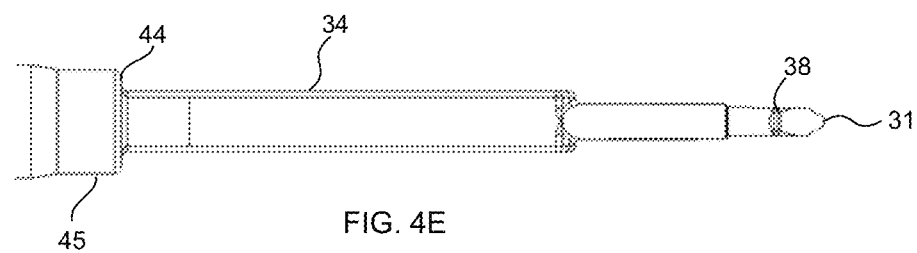
Figure 4F:
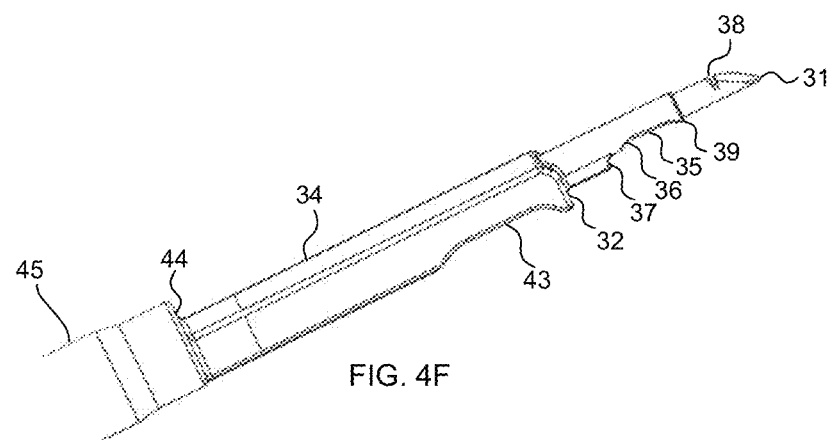

Continuing along the awl 30 from the distal end, shaft 33 continues proximally towards handle 40, as illustrated in FIGS. 3-4F. Proximal of shoulder 32, a distal shaft portion 34 has a generally rectangular profile to generally match the profile of the eyelet 20. Since at least a portion of shaft portion 34 will enter into the bone, having a shape similar to the eyelet may prevent over-enlargement of the bonehole. Distal shaft portion 34 includes a pocket 43 having a distal surface 43a tapering in a first lateral direction, a proximal surface 43b tapering in a second lateral direction opposite the first lateral direction, and a flat surface 43c in between the proximal and distal tapering surfaces and oriented in the longitudinal direction along shaft 33. The taper of distal surface 43a in the first lateral direction is the same lateral direction as the first lateral direction in which barb 23 extends. At least a portion of pocket 43 (e.g., distal surface 43a) coincides, in the longitudinal direction, with the barb 23 which may limit enlargement of the bonehole during passage of barb 23 into the bone and allow for easier passage of the barb into the bone (e.g., past the cortical layer)— further functionality of these corresponding structures is discussed below. Distal shaft portion 34 continues proximally to shoulder 44, which may serve as a stop to prevent over-insertion of eyelet 20 into the bone. Proximal of shoulder 44, a larger shaft 45 continues proximally to handle 40, and ultimately, proximal face 42 of handle 40 against which the mallet or the like may apply the distal force. The handle may also include at least one suture cleat 41 for management of the filament (not shown) passed through the throughbore 25 of the eyelet. Optionally, a second filament (not shown) can be passed through the eyelet and cleated at the handle cleats 41, and not passed through tissue or any other structure, for further securement of the eyelet to the awl, which can be removed when it is desired to separate the awl from the eyelet.

Figure 2D:
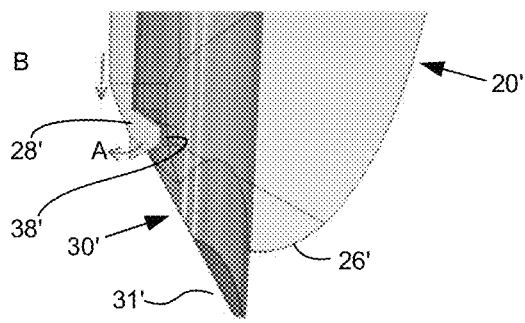
FIGS. 2D-2E illustrate particular aspects of another embodiment of a first fixation member and first inserter of the present disclosure.
Figure 2E:
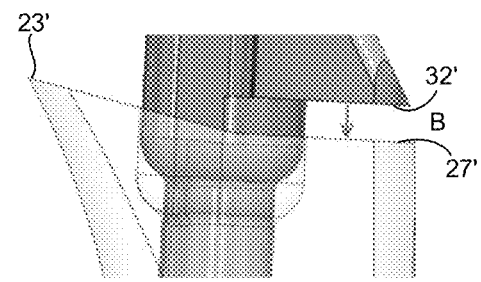

In one exemplary use of this embodiment, eyelet 20 is positioned on awl 30 as illustrated in FIG. 2B, and for illustration purposes, also as shown in FIGS. 2D and 2E as to eyelet 20' and awl 30'. In this position, the eyelet and awl are ready for use and as such are directed by an operator to a surgical site, and more specifically, to a bone in which the eyelet is intended to be used. Deformable portion 28 may maintain eyelet 20 on the awl 30 during pre-surgical activities, and further, can also be useful if the eyelet and awl ever needed to be removed from the patient, such as from a joint space, typically prior to full impaction into the bone, such that the eyelet will remain on the awl while passing through a cannula's diaphragm commonly used in arthroscopic surgery. At least one end of a filament, or of multiple filaments, is positioned through throughbore 25 at a time prior to inserting eyelet 20 into bone—for example, at least one filament is first connected to soft tissue, as known in the art, and at least one end of the filament is subsequently passed through throughbore 25 (e.g., see FIG. 16A). The distal tip 31 is positioned against the bone and the operator initiates formation of the bonehole by application of a distal force to drive the distal tip 31 into the bone. This force is typically applied using a mallet against the proximal end 42 of awl 30, though other methods are also envisioned. At one point during application of this force, typically the first application (e.g., the first mallet strike), the applied force in the distal direction, coupled by the proximal force of the bone surface against the distal end 26 of eyelet 20, causes deformation of deformable portion 28 (illustrated by arrow A in FIG. 2D). This deformation, and the various forces acting on eyelet 20, causes the eyelet to move proximally relative to awl 30 (illustrated by representative length B in FIGS. 2D-E) until proximal end 27 abuts shoulder 32 (FIG. 2C). This relative motion may be fulfilled, for example, upon the first mallet strike such that the eyelet can be readily removed from the awl after a single mallet strike or after multiple strikes, depending on the particular surgical procedure, bone hardness, etc.

With shoulder 32 abutting proximal end 27 (FIG. 2C), continued application of force (e.g., additional mallet strikes) drives awl 30 and eyelet 20 (and attached filament) distally into the bone. Also in this eyelet/awl position, barb 23 coincides with at least a portion of pocket 43, meaning that the combination of barb 23 and distal surface 43a maintains a generally constant width along the longitudinal length of the eyelet 20/awl 30 combined system which is ultimately inserted into the bone (not including the distal-most portion of the eyelet and awl system, in particular distal end 26 and distal tip 31). Put another way, the barb and pocket configuration creates a "pocket-and-push" configuration on the eyelet and awl system, that is, as the width of the eyelet increases, by the lateral extension of the barb 23 in the first lateral direction, the width of the awl decreases by tapering in the first lateral direction along distal surface 43a, which is located on the awl opposite to the barb. Thus, the overall width along the length of eyelet/awl at the increase in the width of eyelet 20 and the decrease in the width of awl 30 relative to the width of the awl and/or eyelet in either direction from the barb and pocket is generally the same (again, other than the distal-most portion of the system, such as distal end 26 and distal tip 31).

This pocket-and-push configuration of this embodiment provides functional benefits to the system. First, it may allow the eyelet 20 to maneuver its way through the bone and provide an opportunity for the barb to catch as much bone material as possible once within the bone. Second, the pocket-and-push features, by allowing lateral movement of the eyelet and awl, help to maintain as narrow an instrument/implant configuration as possible and therefore provide for as narrow a bonehole as possible, particularly through the cortical layer. Continuing with the above example, as the distal tip 31 and distal end 26 continue into the bone, the eyelet and awl move in a generally distal direction into the bone. As the barb 23 approaches the bone, it contacts the cortical surface and its tapered shape tends to apply a lateral force to the eyelet and awl. At this point, without pocket 43 and distal surface 43*a*, this lateral force could result in a larger cortical opening and/or damage to the eyelet. However, the distal surface 43*a* provides the "pocket" on the awl and allows room for the awl and eyelet to shift laterally and allow passage of the barb which may decrease the risk of expanding the bonehole or damaging the eyelet. Once the barb is past the cortical layer and into the cancellous bone, the pocket is shaped to include a tapered surface in the other direction (the second lateral direction), proximal surface 43*b*, which may now "push" the awl and eyelet back in an opposite lateral direction to, generally, its original position relative to the bone. However, with the barb 23 past the cortical layer, the barb may now be positioned underneath the remaining/existing cortical layer around the bonehole. Thus, the effect of this pocket-and-push configuration may serve to ease installation of the eyelet into the bone while also positioning the eyelet in a favorable position, which is already partially underneath the remaining cortical bone and already at least partially engaged with the cancellous bone surrounding the bone hole, to help ensure a successful implantation of the eyelet.

Once at the desired position and depth, since the deformable portion should now be withdrawn from groove 38 and in the release position, proximal motion of awl 30 releases the awl from eyelet 20, such that the eyelet and attached filament remain in the bone and the awl is removed from the surgical site. Optionally, once the awl 30 has been removed from the eyelet 20, the orientation of the eyelet within the bone may be altered, such as, for example, by rotation of the eyelet relative to the bone. With the awl removed, the operator may at any point desired apply tension to the filament positioned through throughbore 25 to set the eyelet and/or to test its position within the bone. Typically, for ease of operation and for efficient suture management, such tension would not be applied until the fixation member 50 is positioned at the bone ready for insertion (as discussed below), though the operator may desire to tension before that step, such as to test the eyelet positioning by tensioning the filament prior to bringing the fixation member 50 into the surgical site. As discussed in greater detail below, the ultimate position of the eyelet may depend on the quality of the bone around the formed bonehole, but typically, the combination of tension on the filament and the engagement of barb 23 with the surrounding bone, results in the eyelet 20 flipping or rotating within and relative to the bone. As such, the eyelet may be positioned transverse to the formed bonehole such that at least a portion of the eyelet may not even reside within the formed bonehole but instead be compressed into the surrounding cancellous bone mass. Next, the method includes implantation of a fixation member, such as fixation member 50, to secure eyelet and filament to bone, which is discussed in detail below.

Turning back to the exemplary embodiment of the implant system of the present disclosure, the implant system also includes, as illustrated in FIGS. 5A-6A, 7A and 8, the second fixation member, illustrated as fixation member 50, and the second inserter, different from the first inserter 30, illustrated as inserter 60.

In one embodiment, as illustrated in FIGS. 5A-E, 6A and 7A, the fixation member 50 is a headless screw, commonly known as an interference screw in the art, and may be cannulated or non-cannulated, and may further be fenestrated. The cannulation and/or fenestrations are intended to reduce implant material volume and allow for blood flow through the fixation member, and the cannulation (whether along only a partial length of the member or completely along the length of the member) can further provide for attachment to the second inserter, illustrated as insertion instrument 60. As illustrated, instrument 60 includes a shaft 61 extending distally from handle 65 to a distal end 62. Fixation member 50 is illustrated as including a cannulation 51 throughout such that fixation member 50 is positioned on shaft 61 and the distal end 62 may or may not protrude distally past fixation member 50. Cannulation 51 and distal end 62 may include a torque-transferring interface, such as, as illustrated, hex-shaped surfaces. Handle 65 may include at least one filament cleat 66 for suture management.

Figure 5A:
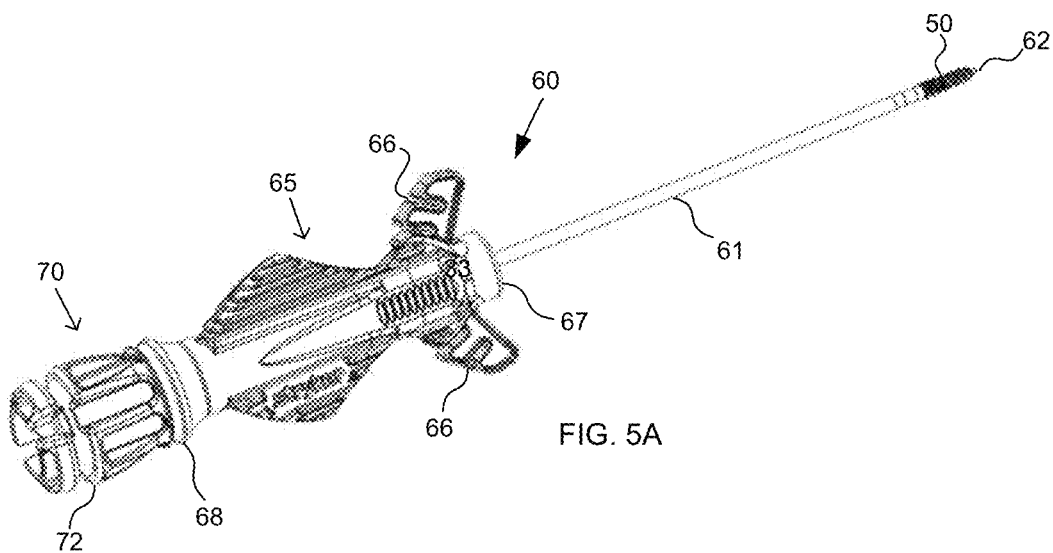
FIGS. 5A-5E illustrate one embodiment of a second fixation member and second inserter of the present disclosure, in particular an inserter and fixation member.
Figure 5B:
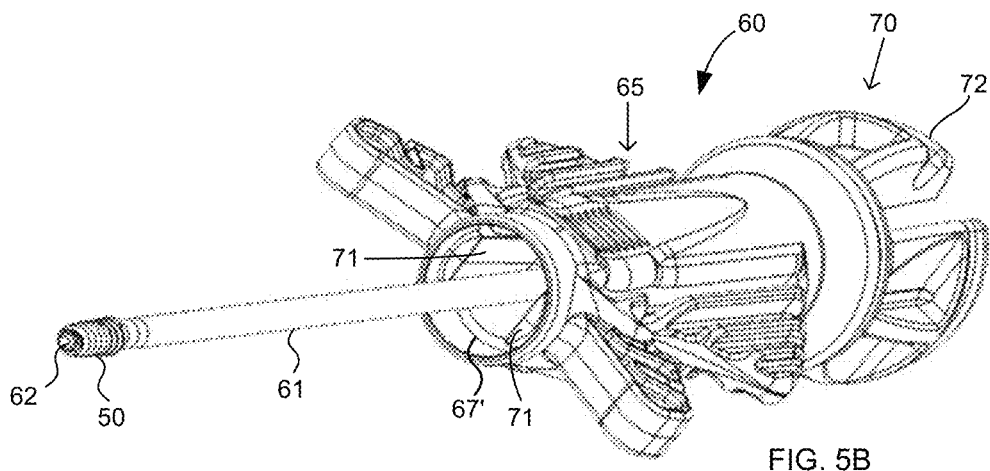
Figure 5C:
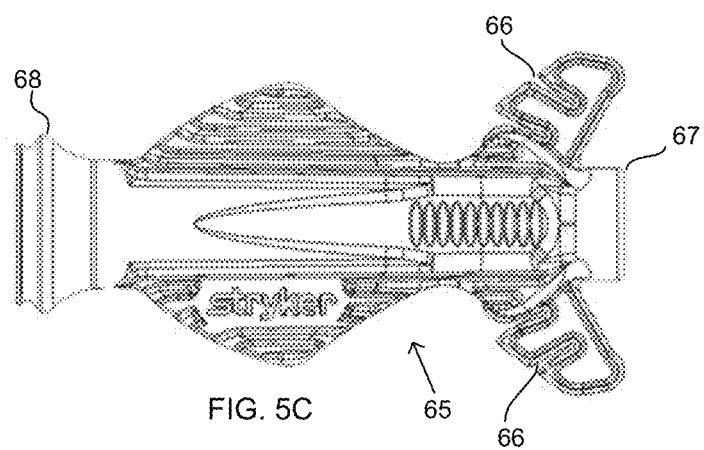
Figure 5D:
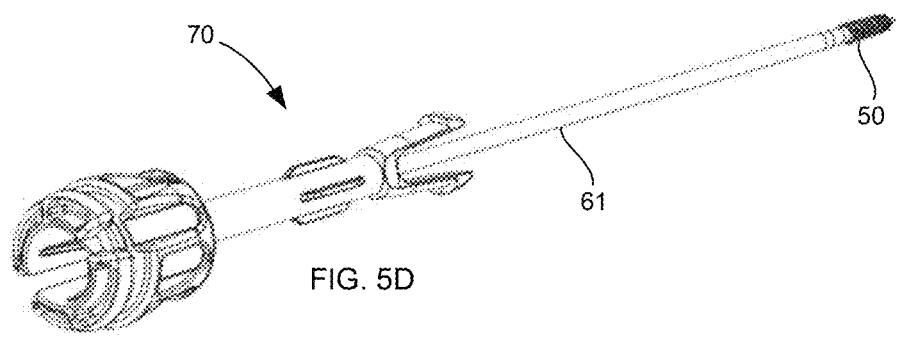
Figure 5E:
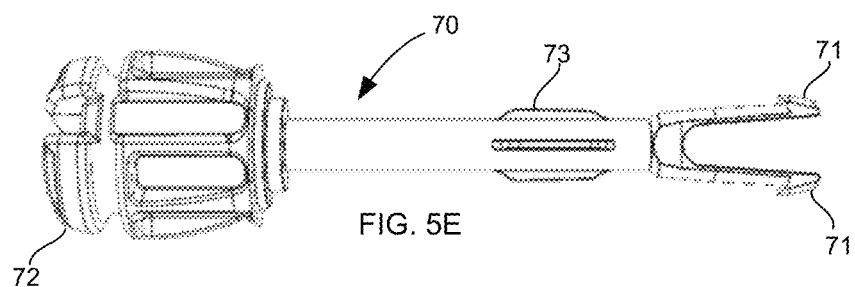

In addition to the shaft 61 and handle 65, instrument 60 also includes torque handle 70 which is engaged with handle 65 to provide a user interface for the operator to handle instrument 60 to implant fixation member 50. FIGS. 5D and 5E illustrate that torque handle 70 is rotatably fixed with shaft 61, such that as the operator rotates knob 72, it imparts rotational torque to shaft 61, and thus fixation member 50 by the interface of the distal end 62 and the cannulation 51 (e.g., as illustrated, a hex-shaped distal end 62 of shaft 61 interfacing with a hex-shaped cannulation 51 of fixation member 50). Handle 70 also includes an interfacing member to maintain engagement with handle 65. For example, as illustrated, the interfacing member may be tabs 71 and groove 67' at distal portion 67 of handle 65, as well as an abutment between knob 72 and proximal portion 68 of handle 65. These interfacing structures may provide, as illustrated, longitudinal fixation (i.e., along the axis of the instrument 60), but relative rotational movement (i.e., around the axis of instrument 60). Thus, in use, an operator may stabilize the instrument 60 by grasping handle 65 and insert fixation member 50 by rotation of knob 72 relative to handle 65. Ribs 73 provide further stabilization of handle 65 on handle 70 during use of the instrument 60.

FIGS. 6B-L and 7B-D illustrate other embodiments of the second inserter and the fixation member, each of which is designated by like reference numbers (e.g., shaft 161, 261, 361, 461, 561, 661, 761, 861 and distal end 162, 262, 362, 462, 562, 662, 762, 862 of instrument 160, 260, 360, 460, 560, 660, 760, 860 and fixation member 150, 250, 350, 450, 550, 650, 750, 850). As illustrated, each of the other exemplary embodiments likewise includes a distal end 62, 162, 262, etc. which extends to or beyond the distal end of the fixation member 50, 150, 250, etc., though a distal end of the instrument which does not extend to or beyond the distal end of the fixation member (i.e., ending proximal to the distal end of the fixation member) is also envisioned. A distal end extending through the entirety of the fixation member may improve torque transfer from the instrument to the fixation member and improve overall strength of the instrument and fixation member. Further, a distal end extending past the fixation member may also assist in guiding the fixation member to the bone hole, assist in navigating within the bone hole relative to the eyelet and suture therein, and the like. Alternatively, a shorter distal tip, whether ending at or proximal to the distal end of the fixation member, may minimize interaction between centrally routed sutures and sharp edges of the distal tip or allow for easier maneuverability within the joint space and may allow for a shallower bore hole to be formed within the bone. Further, the shaft of the instrument, such as for example instrument 760 of FIG. 6H, may be cannulated through at least a portion of its length, or the instrument may not be cannulated, such as for example instrument 860 of FIG. 6I.

Figure 7A:
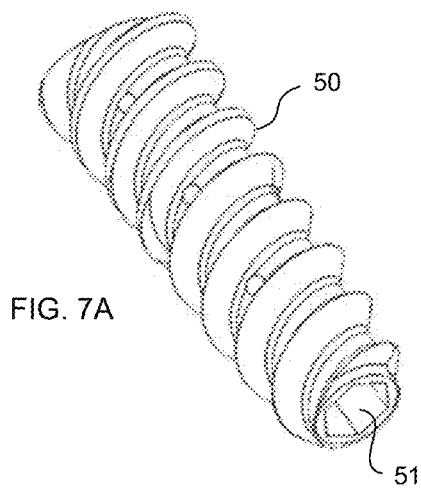
Figure 7B:
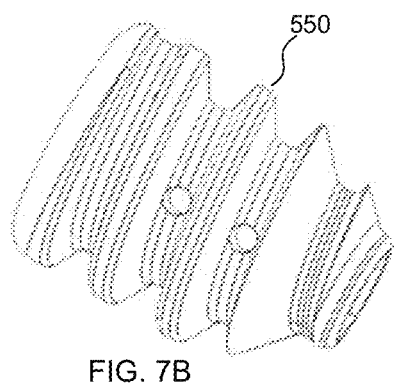
Figure 7C:
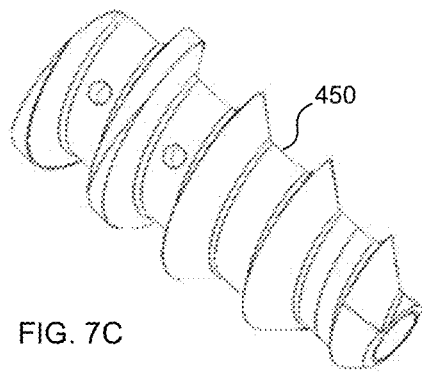
Figure 7D:
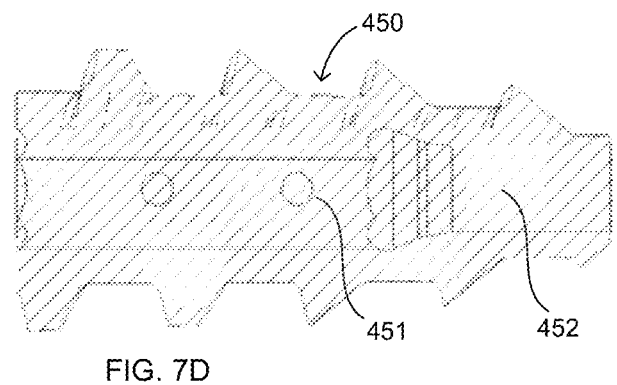

Similarly, the fixation members 50, 150, 250, etc. may be noncannulated (e.g., having a closed distal end and an instrument engagement feature at the proximal end or through a portion of the length of the fixation member) or cannulated and further, such cannulated fixation members may have a constant shape and/or diameter cannulation (e.g., fixation member 50 of FIG. 7A) or the cannulation may change along the length of the fixation member (e.g., fixation member 450 of FIGS. 7C-D). In certain embodiments, such as when used with fixation member 450, the distal end of the instrument may similarly have a distal end having a non-continuous shape, such as distal end 362, 862 of FIGS. 6K-L. The fixation member and instrument used will depend on the desires of the operator and needs of a specific surgical procedure or anatomical location. For example, a noncannulated fixation member may have a tapered tip, which is of a smaller diameter and can be easier to initiate threading into the bone. The fully cannulated version, however, in addition to allowing for improved blood flow, also provides for a stronger connection between the fixation member and the inserter, particularly at the distal end of the fixation member, which may improve implantation capability despite the wider distal tip compared to the non-cannulated version.

Figure 8:
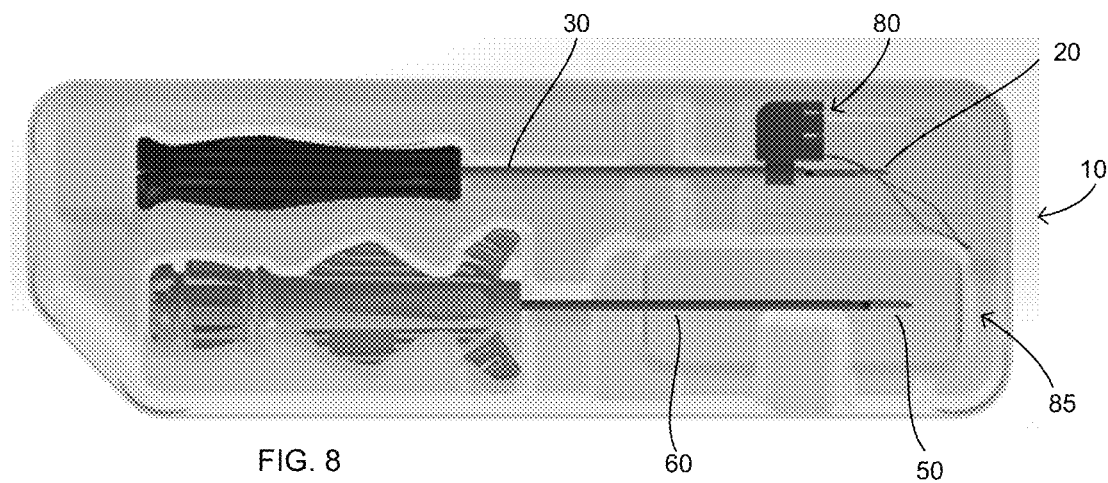
FIG. 8 illustrate one embodiment of a kit and system of the present disclosure, including the first fixation member, first inserter, second fixation member and second inserter of FIGS. 1A-1G, 2A-2C, 3, 4A-4F and 5A-5E.

Turning back to the above exemplary method of use of the implant system of FIG. 8, following positioning of the eyelet 20, and associated filament, in bone, and with the awl 30 removed from the surgical site, the second inserter, instrument 60, with fixation member 50 may be directed to the surgical site, and specifically, to the bonehole formed in the bone. The distal end 62 of instrument 60 may be used to help locate the bonehole and, once engaged, the distal end 62 sits within the bonehole such that the distal end of fixation member 50 contacts the outer surface of the bonehole. The operator may then apply a rotational force to knob 72 to engage the screw threads with the bone and initiate insertion of the fixation member into the bone. At some point before initiation of the rotational force, the filament is tensioned to set the eyelet 20 and move the tissue attached to the filament to a desired location. The tensioning filament may be engaged to cleat 66 for purposes of suture management and to maintain the tension. Continued insertion of the fixation member 50 into the bonehole secures the filament to the bone by interference fit in between the outer surface of the fixation member and the inner surface of the bonehole. Once the proximal end of the fixation member 50 is flush or below the surface of the bone, the repair is complete.

Figure 15A:
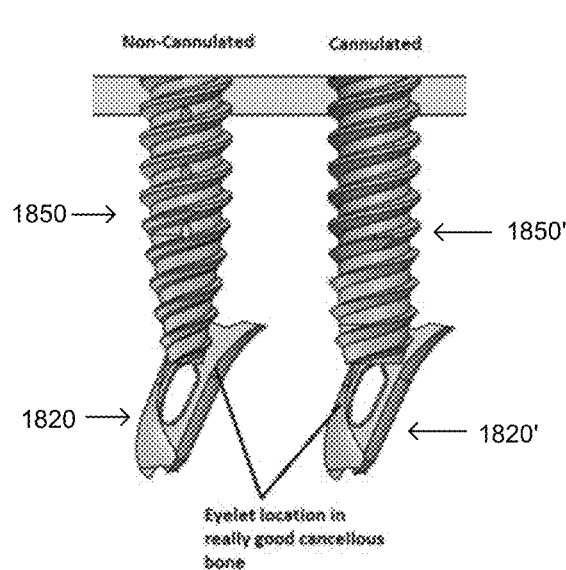
FIGS. 15A-15E illustrate representative configurations of first and second fixation members in various qualities of bone, as well as comparisons to exemplary prior art anchors in similar bone of various qualities.

As discussed above, depending on a variety of factors, including the quality of the bone at the surgical site, FIG. 15A illustrates one example of the positioning of an eyelet relative to a fixation member, such positioning being more typical in higher bone quality, and thus, harder bone. In such instances, any tension applied to the filament and eyelet 1820, 1820', prior to implantation of the fixation member 1850, 1850', may not cause the eyelet to overly migrate or flip, due to the hardness of the bone surrounding the bonehole. In such instances, the eyelet remains generally towards the bottom of the bonehole, and the fixation member moves into place adjacent to it within the bone hole—as illustrated, the eyelet 1820, 1820' moves laterally relative to the bonehole, even in instances of hard bone due at least to the barb on the eyelet, and the fixation member compacts the eyelet between the fixation member and the surrounding bone of the inner wall and bottom wall of the bonehole.

Figure 15B:
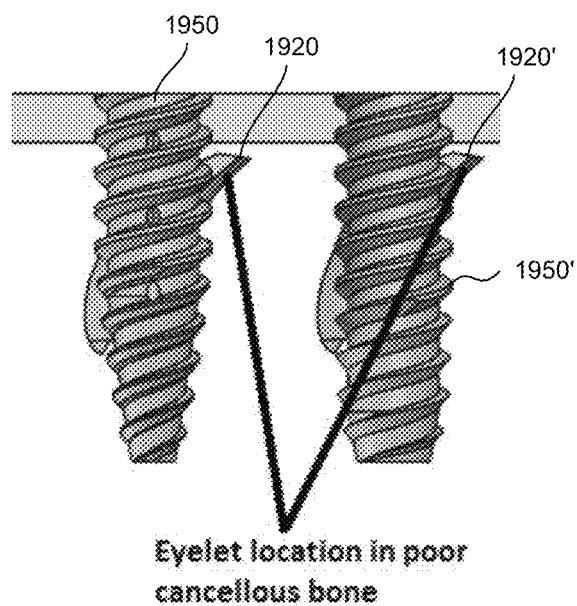

In another example, FIG. 15B illustrates a representative implant positioning in lower quality bone, and thus, softer bone. In this variation, tension on the suture may pull the eyelet 1920, 1920' higher up the bonehole, even to a position where it wedges underneath the cortical layer adjacent the bonehole. Additionally, such tension may result in further rotation of the eyelet. Insertion of the fixation member 1950, 1950' as discussed above thus may position the eyelet lateral to the fixation member and thus within the cancellous bone surrounding the bonehole and/or underneath the cortical bone layer adjacent the bonehole. Such positioning of the eyelet may further improve pullout, which is of particular importance in soft bone.

Thus, the location of the eyelet relative to the length of the fixation member may depend on bone quality—when the cancellous bone quality is good, the eyelet may deploy at its deepest depth, but when the cancellous bone quality is poor, the eyelet may deploy very close to the cortex. This migration in poor bone quality may ultimately be desirable because the eyelet, in such instances, might not provide any additional fixation to the construct when placed down lower in the bone hole. However, with the eyelet positioned adjacent to or against the undersurface of the cortex, the eyelet should be in the best-available bone and, additionally could create a back stop against the underside of the cortical bone layer since the surface area of the eyelet in an angled or rotated position is larger than the opening through the cortical bone layer.

Figure 15C:
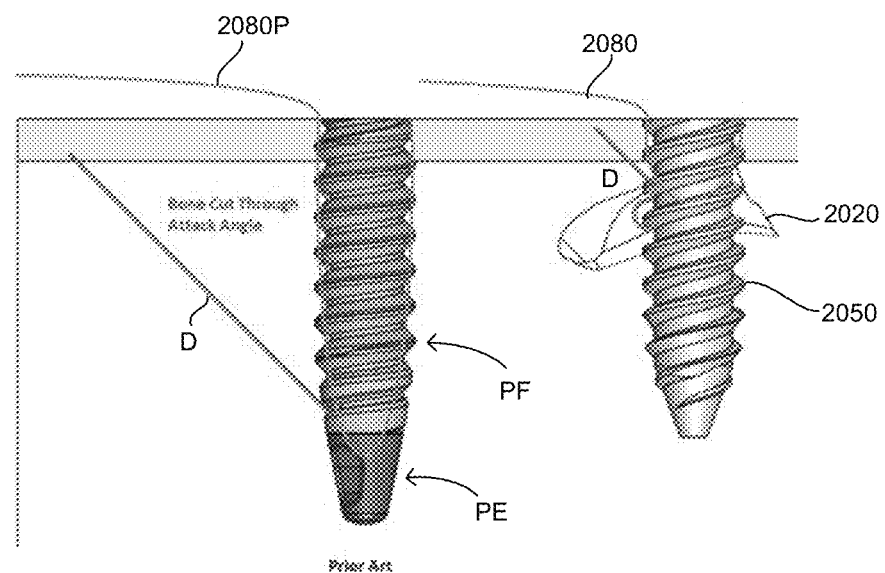
Figures 15D, 15E:
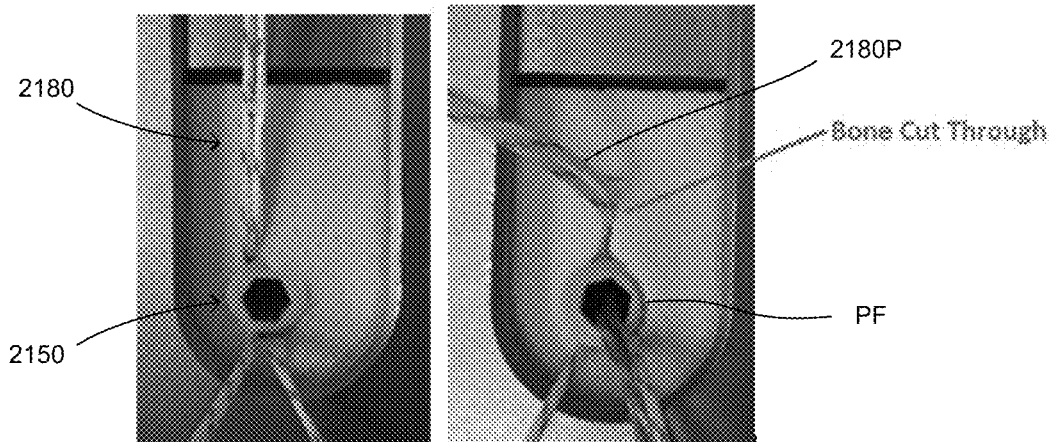

Further, there may be a theoretical advantage of having the eyelet closer to the cortex with regards to a failure mode called "bone cut through". With the eyelet close to the cortex while keeping the "attack angle" the same, the length of cut through would be theoretically less when the eyelet is close to the surface, as illustrated in FIGS. 15C-E. As bone cut through is particularly prevalent in softer, lower quality bone, the migration of the eyelet towards the cortical layer in such soft, low quality bone can be beneficial. FIG. 15C illustrates the decreased cut through D which may occur with eyelet 2020 and filament 2080 versus the larger potential cut through D' due to the positioning of prior art anchor PE and filament 2080P. FIGS. 15D-E illustrate top views of such cut through illustrating the decreased cut through by filament 2180 versus the larger cut through by the prior art anchor PF with filament 2180P. Further, bone cut through can result in loosening of the tension on the attached soft tissue, and thus, the position of eyelet 2020, which is possible since eyelet 2020 is separate from member 2050, can also be beneficial in that any potential loosening of the tension on the filament is minimized, resulting in a superior repair.

Having the eyelet as a separate structure from the fixation member may provide certain additional advantages. For example, in the above-discussed embodiment, the eyelet 20 is positioned on an awl 30 such that, upon forming the pilot hole with the awl, the eyelet is implanted into the newly formed pilot hole. In other words, the eyelet, coupled to the awl, may be self-tapping such that the bone hole is formed as the eyelet is positioned in the bone, though in particularly hard bone, an initial pilot hole and/or removal of the cortical layer may need to be formed prior to use of the awl and eyelet. Optionally, a suture shuttle 80 can be used to assist the user in threading the suture through the eyelet (as illustrated in FIG. 8) such that the awl and eyelet 20 may be packaged with the eyelet 20 on the awl 30 and the suture shuttle 80 positioned through the eyelet and ready for use. A fixation member 50 is then positioned on a separate inserter 60 and can also be included in the packaging with the awl 30 and eyelet 20 (as in FIG. 8). The pilot hole formed using the eyelet 20 and awl 30 of the present invention may be smaller than pilot holes formed by current products on the market, and thus, since less bone is removed, higher fixation strengths can be achieved, resulting in decreased risk of pullout (e.g., fewer instances where the implant sits proud relative to the bone surface) or suture slippage, particularly in lower quality bone.

Further, continuing with this embodiment, the separate eyelet configuration also may allow for a failure mode that is preferred relative to the prior art. In particular, since the eyelet is separate from the fixation member, and sits anywhere within the bone, pullout of the implant is less likely, and as a result, the failure mode is simply slippage of the filament, which is preferred to an implant pulling out and creating a loose foreign object in the patient.

Still further, this embodiment could provide another benefit relative to the fixation member. While the fixation member can be solid or cannulated, in instances where it is cannulated, an eyelet secured to the bottom of the fixation member could block the cannulation, disrupting blood flow therethrough. The separate eyelet of this embodiment, however, allows the eyelet to sit to the side of the cannulation, thereby allowing improved blood flow through the cannulation to promote healing and tissue growth.

Yet another benefit of this embodiment allows for individual selection of an eyelet and a fixation member such that a desired size of each implant can be individually selected. For instance, upon examination of bone quality, the operator (e.g., surgeon) can select an appropriately sized eyelet, and even an appropriately sized awl to form a desired pilot hole. Then, an appropriately sized fixation member can be selected by the operator to ensure sufficient fixation of the repair. Further, if for example, the operator is unsatisfied with the fixation of the selected fixation member, the operator need only remove the fixation member, keeping the eyelet in the bone hole, and select a different fixation member. As such, the modularity of this embodiment provides for increased flexibility for the operator.

In another embodiment, the present disclosure is a method for securing soft tissue to bone using filament, where the tissue is secured without tying knots to secure the tissue to the bone. In this embodiment, filament, such as typical suture or suture tape, is passed through the tissue to be repaired at desired points and one or more suture tails, extending from the tissue, are loaded into an eyelet implant loaded on an eyelet inserter. Once loaded into the eyelet, the tails could be tensioned to remove slack. The eyelet implant is inserted into bone either via a pilot hole or through direct impaction. The eyelet inserter is then removed. A fixation member, loaded on a separate inserter, can then be directed to the bonehole with the eyelet implant positioned therein. The tails can then be tensioned and the fixation member is advanced into the bonehole—the tails can be tensioned prior to or after the fixation member is positioned at the bonehole. With the fixation member in the bone hole, the inserter may then be removed and any loose ends of the filaments protruding from the anchor site can be cut.

Figure 6A:
FIGS. 6A-6L and 7A-7D illustrate various embodiments of second fixation members and/or second inserters.
Figure 6B:
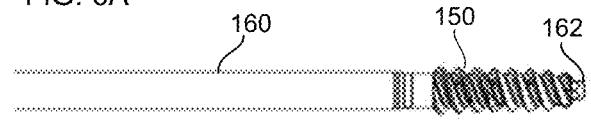
Figure 6C:
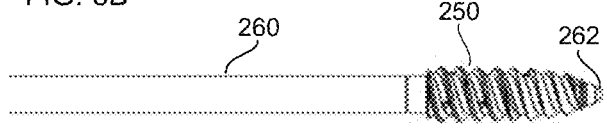
Figure 6D:
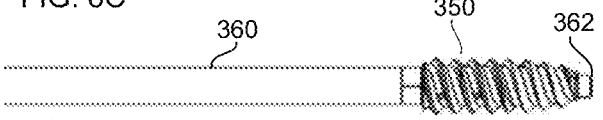
Figure 6E:
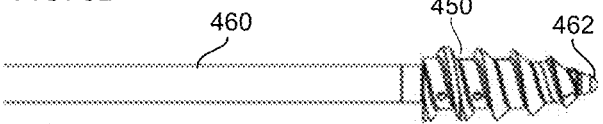
Figure 6F:
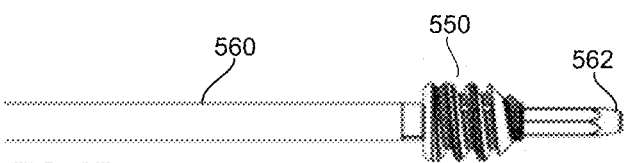
Figure 6G:
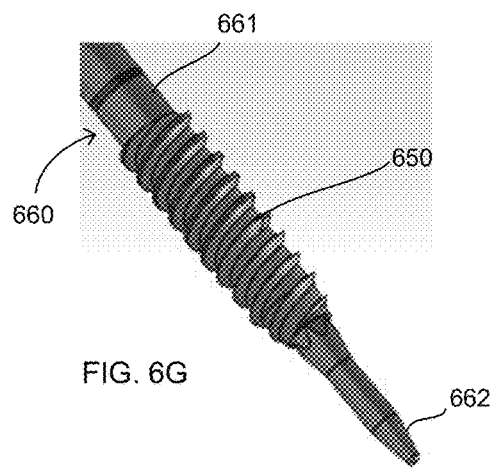
Figure 6H:
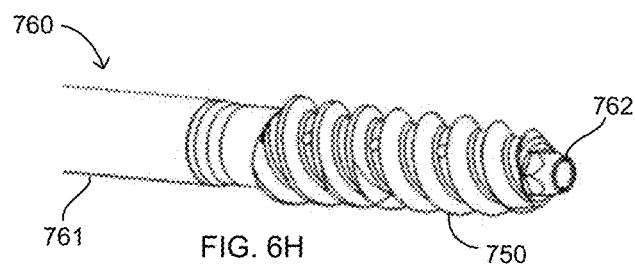
Figure 6I:
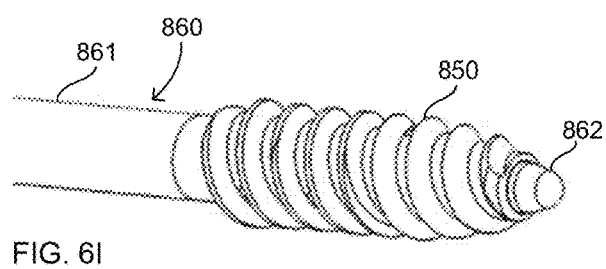
Figure 6J:
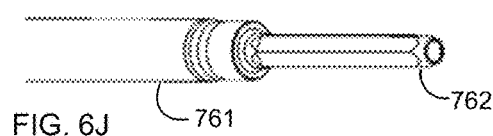
Figure 6K:
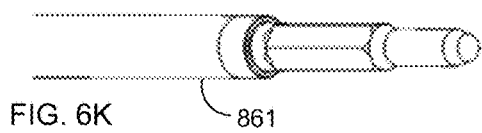
Figure 6L:
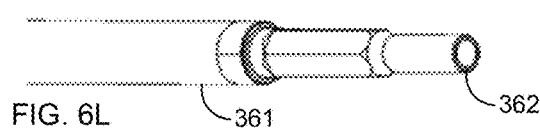

In yet another embodiment, a method of use may be as described above, except that eyelet 20 may include an additional filament passed through throughbore 25. As such, once eyelet 20 is positioned in bone, as discussed above, at least two filaments (and at least one end of each filament) extend from the eyelet and thus, from the bone at the formed bonehole. Referring to FIG. 6H as an example, at least one end of the additional filament, which may or may not be involved in the repair of a tissue, can be positioned up through the cannulation of inserter 760 prior to implantation of fixation member 750. The positioning of an extra filament in this fashion allows for an extra suture to integrate into the repair after the fixation member is in its final position, such as to secure a "dog ear," as is known in the art. Alternatively or in addition, this extra filament can help guide the fixation member 750 and inserter 760 to the formed bone hole and/or locate or retrieve the fixation member once it is dislodged from its inserter and positioned in the bone.

Figure 23A:
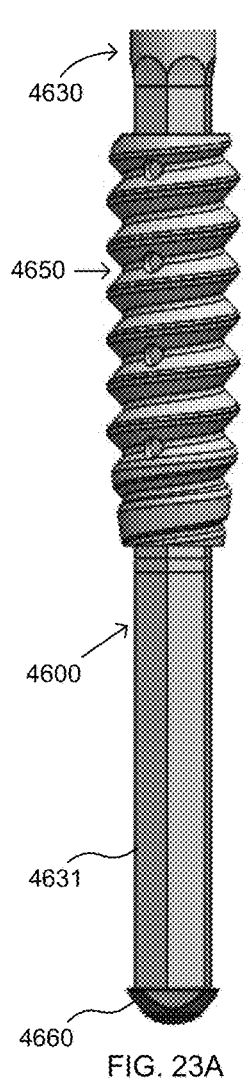
FIGS. 23A-23C illustrate another embodiment of the present disclosure, in particular an inserter, fixation member, and implantable tip.
Figure 23B:
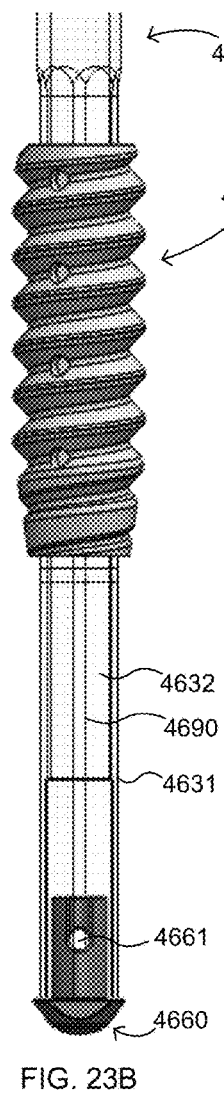
Figure 23C:
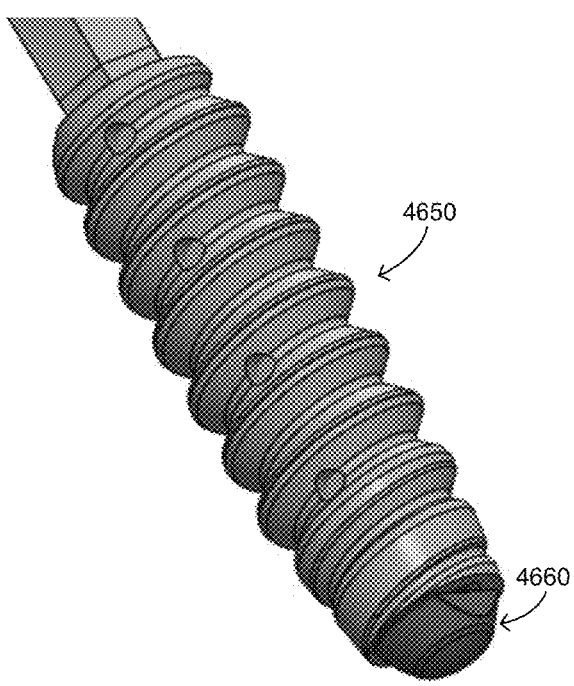

In yet another embodiment, an implantable tip 4660 at the end of a cannulated fixation member inserter 4630, as shown in FIGS. 23A-C, can be utilized for the same reasons listed above, for example, to carry an additional filament 4690 positioned through throughbore 4661 of the tip 4660 to be secured into the bone along with the fixation member 4650. In this embodiment the fixation member would travel down the inserter distal shaft 4631 towards the tip 4660 during fixation member insertion into the bone as with other systems in the prior art. Filament 4690 may be positioned through the cannula 4632 of inserter 4630 for ease of handling by the operator at the proximal end of the inserter. Further, in this position, once the repair is complete, the operator may remove the additional filament 4690 by unthreading it through throughbore 4661.

Figure 16A:
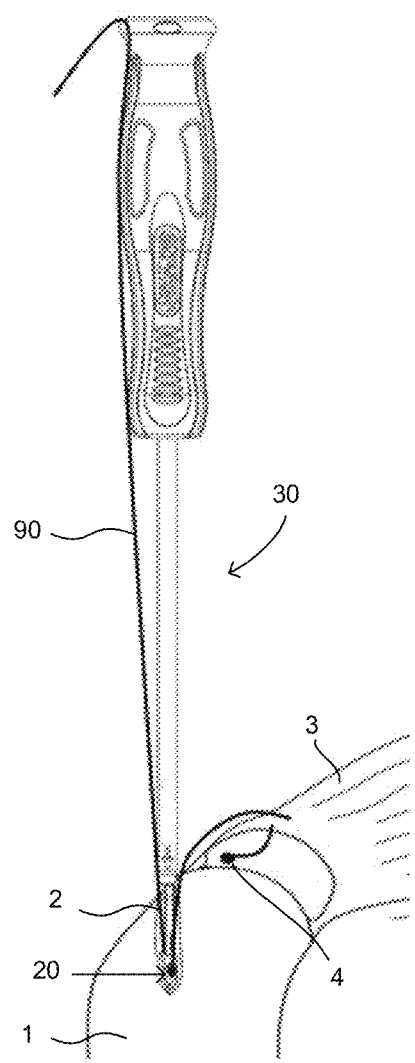
Figure 16B:
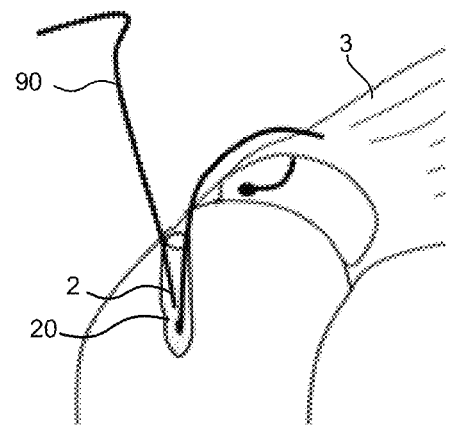

In yet another embodiment, the present disclosure is a method of repairing soft tissue, in particular a rotator cuff in the shoulder of a human patient. As an illustrated example of such a method, FIG. 16A provides awl 30 and eyelet 20, as discussed above, positioned relative to a humerus bone 1 and rotator cuff tissue 3. As illustrated, an optional medial anchor 4 has already been positioned with at least one filament 90 extending therefrom or two ends of at least one filament which has been passed through the tissue and/or medial anchor 4, as known in the art, and a bonehole 2 has already been formed (whether by self-tapping of awl 30 and eyelet 20 or by the initial preparation of the bonehole followed by insertion of the awl and eyelet into the bonehole) for positioning the eyelet 20 (and fixation member 50) as the lateral anchor for filament 90. Further, filament 90 has already been passed through the throughbore 25 of eyelet 20 and eyelet 20 is now positioned at the bottom of the bonehole. FIG. 16B illustrates the eyelet 20 and filament 90 remaining in bonehole 2 with the awl 30 removed (as discussed above). At this point, filament 90 and tissue 3 have not been tensioned, though optionally, the operator at this step may tension the filament 90, and possibly tissue 3 to a desired degree, whether to simply remove slack in the filament 90, to set the eyelet position in the bonehole 2, to cause the eyelet 20 to rotate or otherwise set within the bone 1, or the like. In comparison to prior art utilizing an awl or drill to create a pilot hole for a fixation member, the use of eyelet 20 loaded with repair sutures allows for easier visualization of the pilot hole because the sutures in this embodiment are exiting out of the bonehole and serve as a navigational marker for the operator when directing the fixation member to the bonehole and positioning the fixation member at the bonehole as discussed below.

Figure 16E:
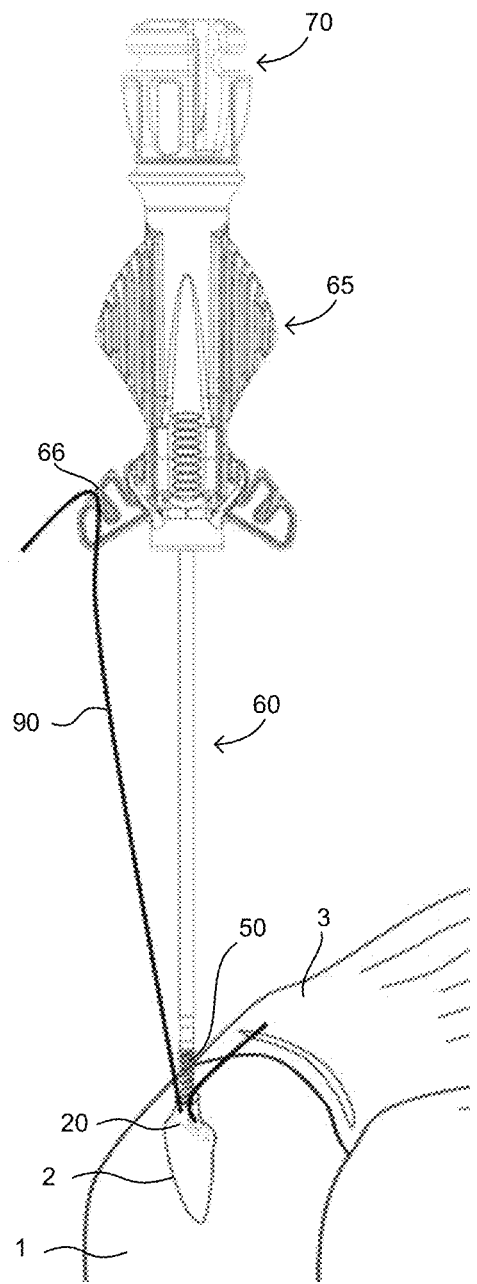
Figure 16F:
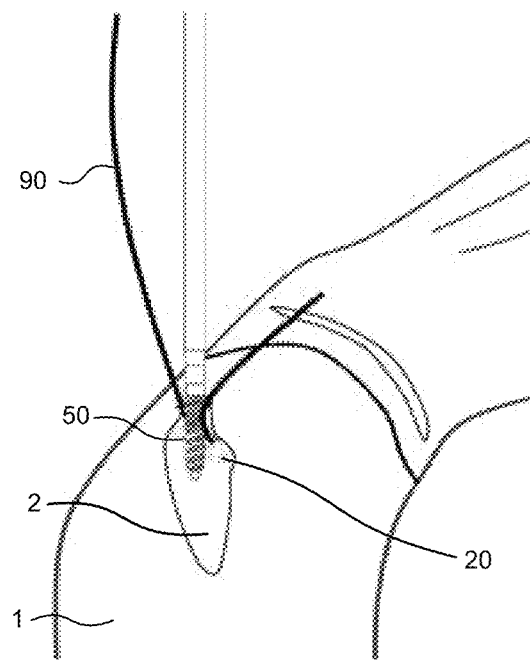
Figure 16G:
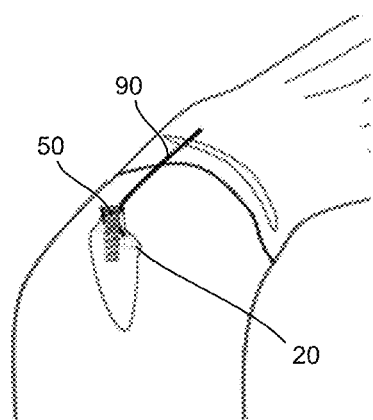

Continuing with this exemplary embodiment, in FIG. 16C, fixation member 50 positioned on inserter 60 is moved into position at bonehole 2 such that filament 90 is positioned between fixation member 50 and the bone first as it extends from tissue 3 and second as it extends out of bonehole 2 and up to handle 65 and the operator. FIG. 16D illustrates the initiation of tensioning of filament 90 which starts to pull tissue 3 laterally, as illustrated by the arrows on tissue 3. At this point, the tension on filament 90 may not have been sufficient to alter the position of eyelet 20. FIG. 16E illustrates continued tension on filament 90 which is shown to reduce the tear in tissue 3 and set the eyelet within the bone 1. Eyelet 20 migrates through the bone 1, which as shown is weak or softer bone, and comes to rest at a position at least partially under the cortical layer. If a cleat is present on the eyelet (as discussed herein), this tension may also set the filament within the cleat. Once the desired tension is reached, filament 90 may be cleated at cleat 66 on handle 65 to maintain the tension while the knob 70 is rotated to drive fixation member 50 into place, as illustrated in FIG. 16F. Fixation member 50 enters bonehole 2 adjacent to eyelet 20 such that eyelet is positioned lateral to fixation member 50 and at least partially under the cortical layer. With the fixation member 50 in place in the bone 1, the filament 90 is clenched between the bone 1 and the fixation member 50, at which point, filament 90 can be removed from cleat 66 and the excess can be cut or otherwise removed, leaving the completed repair illustrated in FIG. 16G.

Figure 16H:
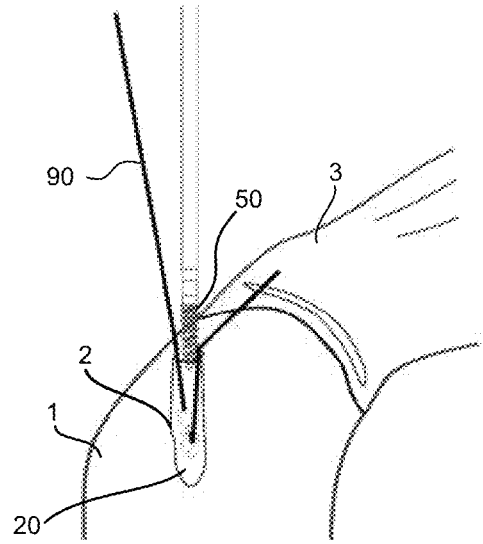
Figure 16I:
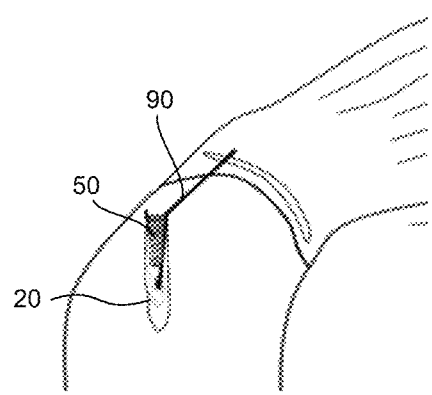

FIGS. 16H and 16I illustrate an alternative exemplary method, where the repair is performed in hard bone 1. As above, tension is applied to filament 90, which reduces the tissue tear 3 and tensions the filament 90 extending through the eyelet 20 to set the eyelet 20 within the bone, as discussed at length above. If a cleat is present on the eyelet (as discussed herein), this tension may also set the filament within the cleat. As this alternative is performed in hard bone 1, FIG. 16H illustrates that eyelet 20 would tend to remain towards the bottom of the bonehole 2. At this point, filament 90 may be temporarily secured in cleat 66. Fixation member 50 may then be driven into the bone 1 as discussed above. FIG. 16I illustrates the resulting repair, where the eyelet 20 has remained towards the bottom of bonehole 2, and has not been able to alter the surrounding cancellous bone to position itself under the cortical layer as in the softer bone of FIG. 16G, though as this bone is much harder, the eyelet 20 of FIG. 16I is securely positioned without meaningful proximal migration towards the cortical layer. Once again, however, eyelet 20 may be positioned at least partially laterally of the longitudinal axis of the fixation member, and even the bonehole 2, such that it may be wedged between the fixation member 50 and the surrounding bone 1.

Similarly, the separate eyelets and fixation members, and respective awls and inserters, can also provide various packaging options which can form various kits. For instance, as illustrated in FIG. 8, a kit 10 includes a single awl 30 packaged with at least one eyelet 20, and a single inserter 60 can be packaged with at least one fixation member 50, as illustrated in FIG. 8. The kit may also include, as illustrated, a suture shuttle 80, as known in the art, for passing a filament through the throughbore 25 of eyelet 20, all of which can be contained in a single package or tray 85, though at least one of the components can be packaged separately. Of course, in an alternative arrangement of a kit, an awl, an inserter, one or more eyelets and one or more fixation members can all be packaged in a single package but brought together and used as a complete system. Still further, more than one awl and/or more than one inserter can also be packaged together, with or without the implants, to provide an operator with different sizes of the instruments and implants. Further, any kit of the present disclosure may include a surgical procedure or instructions which may include step-by-step instructions for performing any of the methods disclosed or implied herein. Other kits and packaging configurations are also envisioned.

In another embodiment, the present disclosure includes a system or kit for the repair of soft tissue including at least one fixation member, at least one inserter, and a surgical procedure. The surgical procedure may include instructions or protocol for using the fixation member(s) and inserter(s).

In an associated embodiment, the present invention includes a method of providing instructions or information to practice any of the various methods described herein. For example, the method may include supplying a surgical protocol, or like document, to provide step-by-step instructions for performing any of the method embodiments of the present invention.

In another embodiment, FIGS. 9A-9C illustrate an eyelet 20', 120' and awl 30', 130' which are largely similar to eyelet 20 and awl 30 discussed above (and thus like reference numbers reflect like structures, such as throughbore 25 and throughbore 25', 125'). However, distal tip 31', 131' and cannulation 24', 124' are generally cylindrical, and thus, eyelet 20', 120' and awl 30', 130' may not be rotationally fixed to one another along these structures. However, eyelet 20' also includes an alignment feature 22' which mates with alignment feature 33' on awl 30' which may prevent relative rotation between the two structures. Eyelet 120' and awl 130' similarly include alignment features 122', 133'.

In other embodiments, illustrated in FIGS. 10A-D, the eyelet 1020, 1120 includes at least one barb, illustrated as arms 1023, 1123, 1123', which are shaped such that the arms sit just below the surface of the bone (e.g., under the cortical bone layer) once implanted and may create a shoulder or stop surface against the underside of the cortical layer. FIGS. 10C-D further illustrate a fixation member 1050 to show its positioning relative to the eyelet 1020, 1120. Eyelets 1020, 1120 include a throughbore 1025, 1125 and a proximal-facing surface 1027, 1127 and a distal end 1026, 1126, all of which are similar to the respective elements above, and rib 1021, 1121, as discussed below.

Figure 11A:
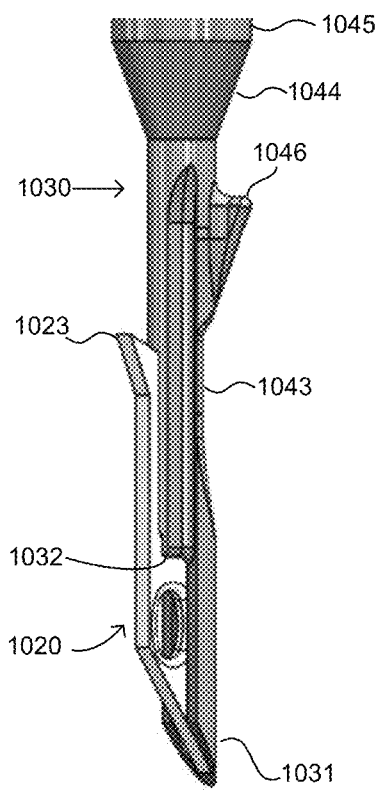
Figure 11B:
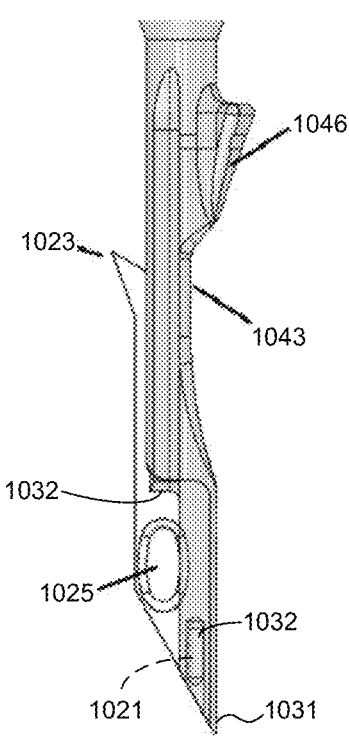
Figure 11C:
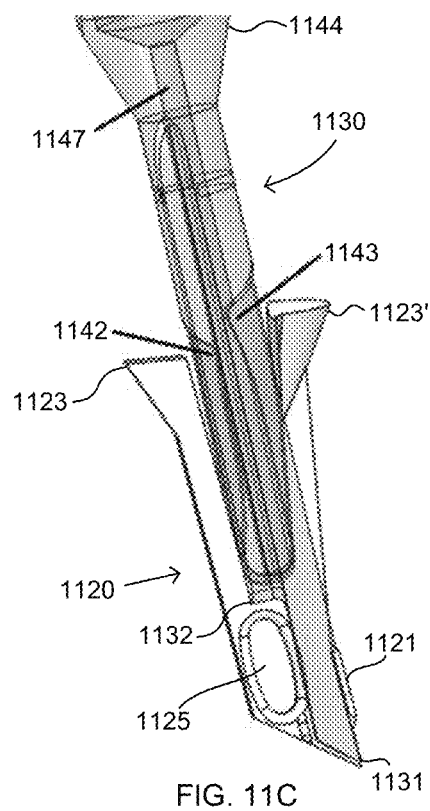

Continuing with these embodiments, eyelets 1020, 1120 are inserted using a first inserter, as illustrated in FIGS. 11A-C as awl 1030, 1130. Instead of passing through a cannulation in the eyelet, the awls of these embodiments are positioned around the eyelet such that distal tips 1031, 1131 include mating grooves (no shown) that correlate with ribs 1021, 1121 to maintain the eyelet on the awl. Also in these embodiments, the distal end 1026, 1126 and distal tip 1031, 1131 together form a leading edge to facilitate formation of the bonehole.

Still further, awl 1030, 1130 includes shoulder 1032, 1132 adapted to impart a distal force against proximal-facing surface 1027, 1127, as discussed above relative to shoulder 32 and proximal end 27 of eyelet 20. Also similar to the above-described embodiment of eyelet 20 and awl 30, awl 1030 similarly includes a pocket 1043 tapering in a first lateral direction, coinciding with barb 1023 and a proximal surface 1046 tapering in a second lateral direction opposite the first lateral direction, which together form the pocket-and-push configuration discussed above. Proximal to pocket 1043 includes shoulder 1044 and larger shaft 1045, also similar to respective structures discussed above as to awl 30.

Similarly, the awl 1130 as illustrated includes a first pocket 1142 for barb 1123 and a second pocket 1143 for barb 1123'. However, contrary to such pockets and barbs described above, the pockets of this embodiment allow for the inward deflection of barbs 1123, 1123' into the pockets 1142, 1143. For example, during implantation of eyelet 1130 into bone, the outwardly tapered barbs 1123, 1123' may contact the bone and, due to the presence of the pockets 1142, 1143, may be allowed to deflect inwardly such that the overall width of the awl and eyelet may remain generally constant, even while the barbs are passing into the bone. Once the barbs pass, for example, the cortical layer, the barbs may return to their outwardly-biased position. In this outward position, the relatively flatter proximal-facing surface of each barb 1123, 1123' may prevent backout of the eyelet by contacting the undersurface of the cortical layer, particularly upon tensioning of the filament positioned through throughbore 1125. Alternatively, in the event the barbs do not return fully to outwards positions, such as in instances of particularly hard bone, a push rod can travel through a push rod cannulation 1147 in the awl and can contact inner surfaces of the barbs, since the cannulation 1147 passes through at least a portion of the pockets 1142, 1143, such that the barbs are forced out manually. In either event, once the barbs return to their outward position, and are thus underneath the cortical layer, the awl can then be removed by pulling or by the use of, for example, a slap hammer or the like.

Figure 12:
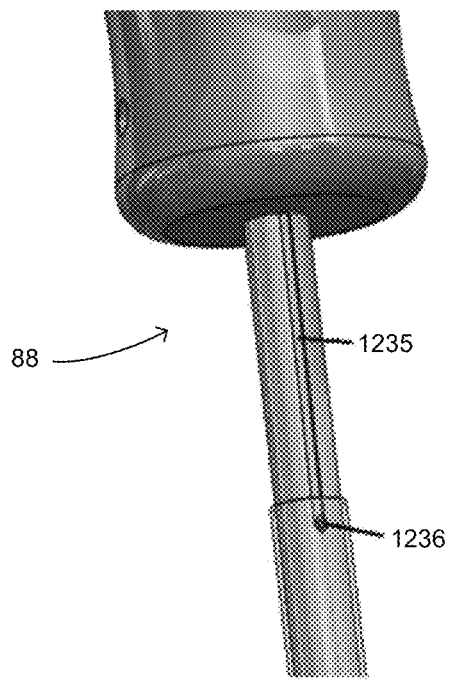
FIGS. 12-14G illustrate further embodiments of first fixation members and/or first inserters.

In addition to, or as an alternative to, the above deformable retention feature, the awl can also include a protector tube, one embodiment of which is illustrated in FIGS. 9C and 12 as protector tube 88. The protector tube 88 may be translatable on the shaft of the awl, such as shaft 33 of awl 30, such that it can be positioned, at a distal position, over the awl 30', and even over at least a portion of or the entirety of the eyelet 20' and, at a proximal position, at least proximal to the eyelet, such that the eyelet is exposed, and even exposing at least a portion of awl 30'. The protector tube, in its distal position over the eyelet, may prevent forces being applied to the eyelet which could cause it to disengage from the awl or cause damage to the eyelet—for example, during movement into the surgical site and towards the surface of the target bone, by the barb engaging bone unintentionally or engaging the aforementioned cannula diaphragm (e.g., particularly where the eyelet and awl need to be removed from the surgical site and back through the diaphragm).

In this embodiment, the tube 88 has at least one dimple 1236 that lives within a respective groove 1235 machined into the proximal portion of the shaft of the awl. The dimple can simply reside in the groove passively, such that the distal portion of the tube 88 can freely slide depending on manual forces applied to it, or the dimple may be movable between one or more set positions along the length of the groove. For example, in one type of use, the tube 88 can passively shift proximally up the shaft as the awl moves distally down through the surgical cannula because, as the awl 30' is pushed towards the bone, the tube 88 is contacted by the cannula diaphragm. This friction holds the tube 88 in place while the awl 30' moves distally, thereby exposing the eyelet (and potentially at least part of the awl) as it approaches the bone into which it is to be inserted. This movement of the tube also may allow for visualization of the eyelet for observation by the operator. Additionally, if it is necessary to remove the eyelet and awl from the cannula, the shaft of the awl would shift back proximally, as the operator pulls it backwards and away from the bone, while the cannula diaphragm holds onto the tube until the dimple hits the bottom of the groove at which point the tube 88 is once again at the distal position to protect the eyelet (including the barb) from interacting with the cannula diaphragm or surrounding tissue while the system is being removed from the patient.

Alternatively, rather than friction on the cannula diaphragm, the tube 88 may be positioned by simply resting against the bone such that the awl and eyelet can simply slide distally relative to the tube and into the bone. Preferably, in this alternative, tube 88 would be translucent (or at least the distal portion of the tube would be translucent) such that viewing of the awl and eyelet entering the bone is possible.

Figure 13:
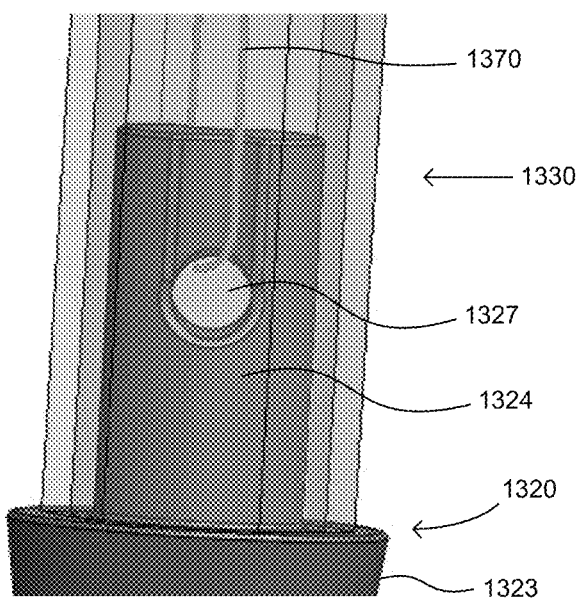

As an alternative to the deformable retention feature and/or the protector tube, the more traditional method of temporarily attaching an implant to the tip of an inserter may involve the use of a retention suture, one embodiment of which is illustrated in FIG. 13. This is possible with an inserter 1330 of the present disclosure but generally requires an extra component (e.g., the suture 1370), a hole 1327 within the eyelet 1320 (which may potentially result in decreased strength), and/or cannulation of the eyelet insertion instrument 1330 or awl and/or suture running up the side of the awl (which can hinder visualization of insertion depth indicators, and further may result in not as "clean" of an appearance commercially). As illustrated, eyelet 1320 includes a projection 1324 extending proximally from the wider portion 1323 (similar to aforementioned barbs) for positioning the suture 1370 through hole 1327. Alternatively, one of the aforementioned eyelets may utilize this additional suture as well, for example, where the suture 1370 may be passed through the throughbore 25 of eyelet 20. In this alternative, the suture would likely need to extend along the outer surface of awl 30 and back to the operator. In any embodiment using such an additional suture, once the eyelet is in position, whether at the bone or at least partially inserted into the bone, the suture 1370 would typically be removed from the eyelet by the operator pulling on one end or integrated into the repair as mentioned earlier.

FIGS. 14A-G illustrate various embodiments of an eyelet having a cleat. For example, eyelet 1320 (FIG. 14A) includes a cleat 1380 in communication with throughbore 1325. As illustrated, cleat 1380 is positioned proximal to throughbore 1325 and includes a distal, wider portion 1382 and a proximal, narrow portion 1381, such that the cleat is "stepped." The stepped structure allows for areas for cleating filaments of various dimensions, and further, can provide for gradually increased tension to the filament. In use, with the eyelet positioned in the bone (as discussed above), and upon tensioning of the filament positioned within the throughbore 1325, the applied tension may draw the filament proximally and into the cleat 1380, first into the wide section 1382 and potentially into the narrow section 1381, if the filament is of a diameter capable of fitting into that area of the cleat.

Figure 14A:
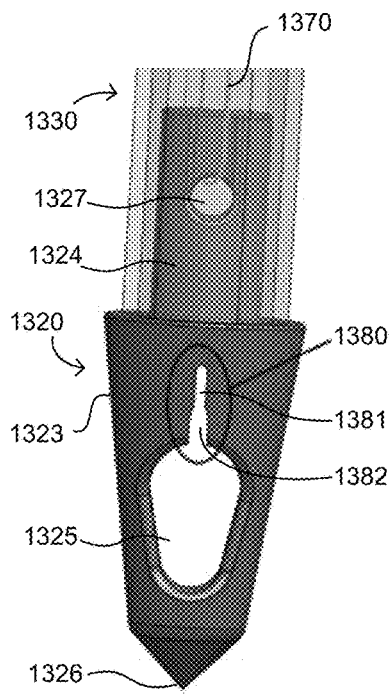
Figure 14B:
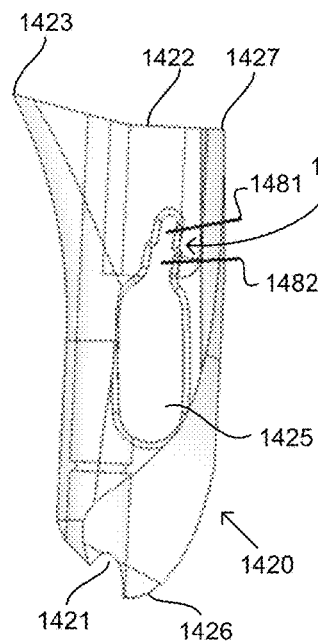
Figure 14C:
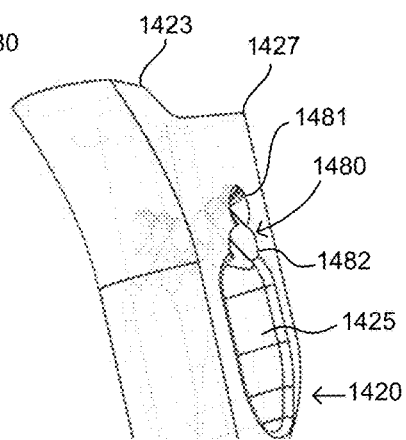

FIGS. 14B-C illustrate another embodiment of a cleat. In this embodiment the cleat 1480 of eyelet 1420 is similarly positioned proximally to and in communication with the throughbore 1425. The cleat 1480 also has a surface texture through both the wider and narrow sections 1482, 1481, respectively, similar to a "boat cleat." The illustrated texture is "ribbed" such that the surface texture provides areas of increased holding force at the peaks of each pair of ribs. Cleat 1480 is also positioned at an angle relative to the longitudinal axis of the eyelet 1420, as best seen in FIG. 14B. The angled positioning, particularly as it is angled in a direction away from barb 1423, may provide additional impetus to cause the eyelet to rotate within the bone. Specifically, the tension on the filament, as it enters the cleat 1480, may cause the eyelet 1420 to rotate slightly, pushing the barb 1423 outwards and against the bone surrounding the bonehole, which in turn generates additional rotational force on the eyelet.

In other embodiments, as illustrated in FIGS. 14D-G, the cleat may be "blocked" during impaction of the eyelet and awl into the bone because if the sutures are cleated (and thus tight between the tissue and the cleat) during the impaction it could lead to "bone cut through" where the sutures cut through the bone since they have no way to go slack as the eyelet is inserted into the bone. As such, blocking the cleat at least during the impaction step allows the suture, connected to the tissue, to travel freely through the eyelet during the impaction step. The "blocking" can be accomplished in a variety of ways, a few of which are illustrated herein.

Figure 14D:
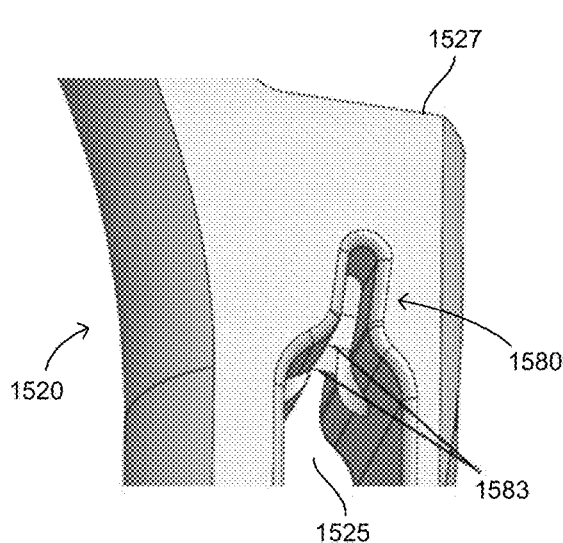
Figure 14E:
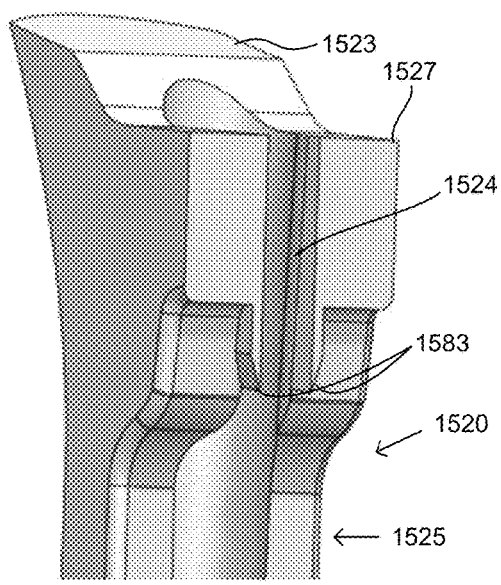

For example, FIGS. 14D-E illustrate yet another embodiment of a cleat. In this embodiment the cleat 1580 of eyelet 1520 is again positioned proximally to and in communication with the throughbore 1525. Cleat 1580 includes a thin wall feature 1583 which is sized to allow for suture to cut through it such that it serves as a cleat. The wall(s) 1583, like the rest of the eyelet 1520 (and indeed, all of the eyelets disclosed herein) may be made from a biocompatible material, such as PEEK, and may be sufficiently sized such that it is weak enough to allow the filament, upon tensioning of the filament (e.g., sliding filament through the eyelet), to cut through the thin wall(s) but strong enough to create supplemental retention force on the suture as a functional cleat.

Figure 14F:
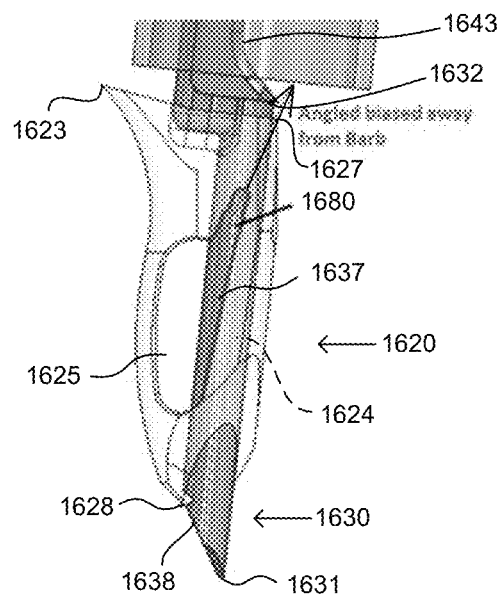
Figure 14G:
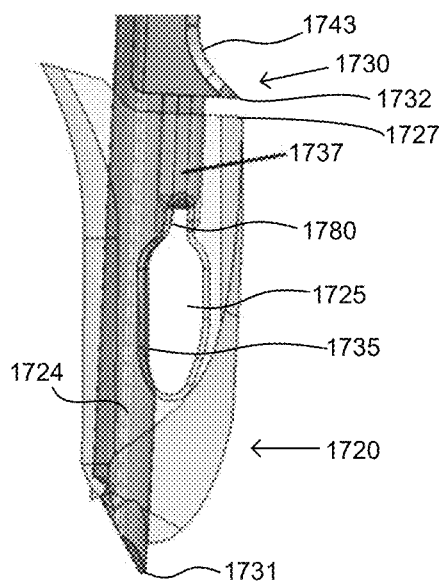

FIGS. 14F-G illustrate exemplary embodiments of the awl 1630, 1730 establishing the "blocking" element of the cleat 1680, 1780 of the respective eyelet 1620, 1720. In these examples, the awl, positioned through a cannulation 1624, 1724 in the eyelet, passes through the volume of the cleat to prevent suture from migrating into the cleat while the awl is in position. Further, FIG. 14G illustrates a variation of "blocking" the cleat whereby, upon initial impaction, the gap between shoulder 1732 and proximal end 1727 (as discussed above) is closed and the blocking feature 1737 on the awl moves into the volume of the cleat to prevent migration of the suture into the cleat until after awl has been removed from the eyelet. Other cleats and blocking features are discussed below relative to FIGS. 18A-19.

Such cleats may offer additional fixation strength of the suture and the overall repair (discussed further below). For instance, the cleat may increase frictional forces holding the filament (e.g., suture, and any tissue which may be attached by the suture) relative to the eyelet. The illustration below shows an eyelet with such a cleat, as well as the aforementioned retention suture to attach the eyelet to the inserter.

Figure 17A:
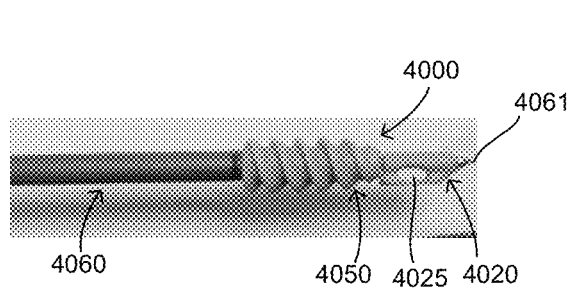
FIGS. 17A-17B illustrate two embodiments of the present disclosure, in particular, of an implant and an inserter.

FIGS. 17A-20C illustrate various embodiments of an eyelet and fixation member where the eyelet and fixation member are connected or otherwise engaged with one another prior to, during, and following implantation into a bonehole. For example, FIG. 17A illustrates one implant 4000 positioned on a single inserter 4060. Implant 4000 includes eyelet 4020 having throughbore 4025, as discussed above, and fixation member 4050. Both eyelet and fixation member are cannulated to allow passage of distal tip 4061 of inserter 4060 to pass therethrough. Eyelet may be rotationally movable relative to the fixation member while on the inserter 4060. Such relative rotation may be useful particularly during implantation of fixation member 4050, which requires threading into the bone, and thus rotation of the fixation member and the inserter 4060. The eyelet can remain stationary during this implantation step to reduce the chance that the suture will wind around the fixation member. Eyelet and fixation member may be held by distal tip 4061 in a variety of ways, such as a frictional or interference attachment. For instance, the eyelet 4020 can be affixed to inserter 4060 with a high degree of friction since the fixation member is present to engage bone and allow for removal of the eyelet along with the fixation member in a single step.

Fixation member 4050 can be positioned anywhere along the shaft of inserter 4060, as desired, such that, for example, a gap exists between member 4050 and eyelet 4020. As such, this embodiment of FIG. 17A may have a configuration where the member 4050 is spaced proximal to eyelet 4020, such that during insertion, with the eyelet positioned in a bonehole, the member 4050 would be inserted into the bone by rotation of the member 4050 (to engage its outer threads with the bone) such that it migrates along the shaft of inserter 4060 towards eyelet 4020, as is well known in the art. Such a configuration and relative motion may, for example, be as shown in FIGS. 23A-C where instead of tip 4660, an eyelet (as disclosed herein) may be positioned at the distal tip of the inserter 4630. However, unlike other systems known in the art, fixation member 4050 and eyelet 4020 may both be formed entirely of PEEK, which is possible due to the configuration of both member 4050 and eyelet 4020 being cannulated such that distal tip 4061 passes through both implants and functions as a self-tapping tip for forming a bonehole.

Figure 17B:
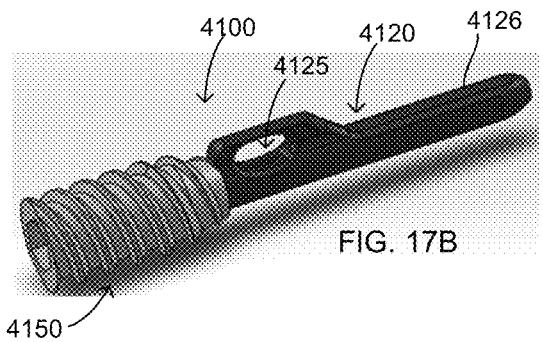

The embodiment of FIG. 17B is similar to that of FIG. 17A, however eyelet 4120 includes a longer distal portion 4126 extending distally of throughbore 4125. This lengthened distal portion 4126 may provide for added utility for the operator since this portion of the eyelet can be inserted into bone while the throughbore 4125 remains proud, thereby allowing suture manipulation or other such adjustments to the implant system while the eyelet is firmly situated relative to the bone. In addition, the shape of eyelet 4120 can allow for suture tensioning to be completed prior to insertion of eyelet 4120 such that the slack created in the suture from impaction of the eyelet is perfectly tensioned upon final repair due to the length of member 4150 being inserted.

Figure 18A:
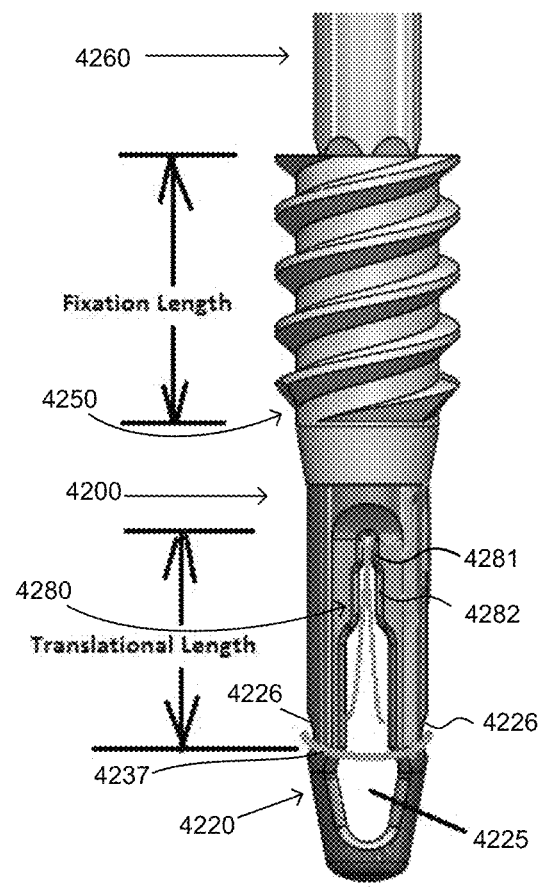
FIGS. 18A-18E illustrate another embodiment of the present disclosure, in particular, of an implant and an inserter.
Figure 18B:
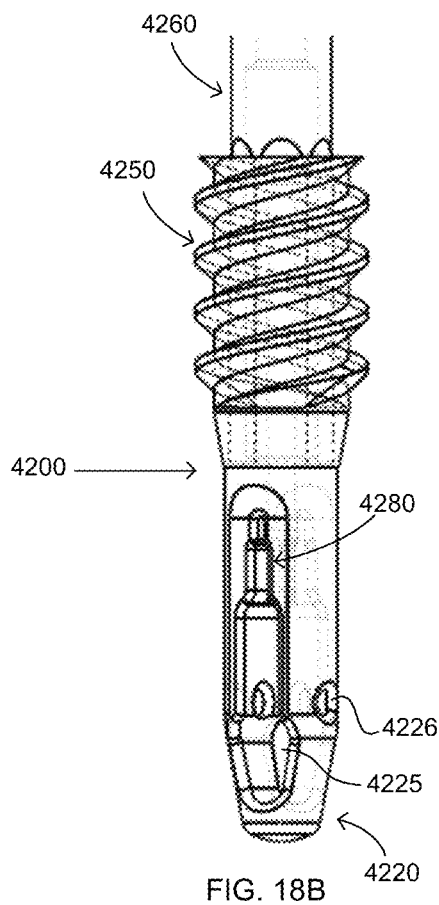
Figure 18C:
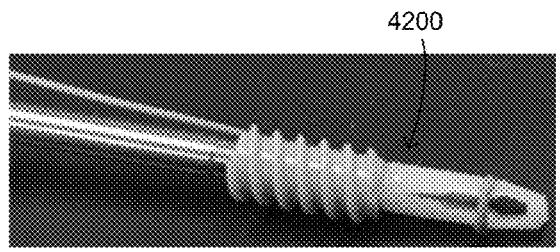
Figure 18D:
Figure 18E:
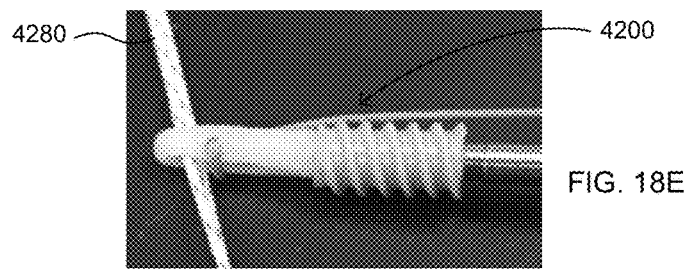

FIGS. 18A-B illustrate another embodiment where an eyelet 4220 and a fixation member 4250 are positioned together as an implant 4200 on inserter 4260. Fixation member 4250 is cannulated such that inserter is positioned therethrough to engage eyelet 4220. Eyelet 4220 includes throughbore 4225, as discussed above. Additionally, this embodiment is illustrated with transverse bores 4226 such that a blocking suture 4237 may be positioned therethrough. As discussed above, blocking suture acts as a blocking feature to prevent a filament, positioned through throughbore 4225 to migrate proximally to a cleat 4280 prematurely. Suture 4237, loops around the eyelet 4220, through bores 4226, and up through a cannulation in the cleat 4280 and ultimately through the inserter 4260 and back to the operator. If present, the suture 4237 may be secured to a cleat on the proximal handle of inserter 4260.

Figure 20A:
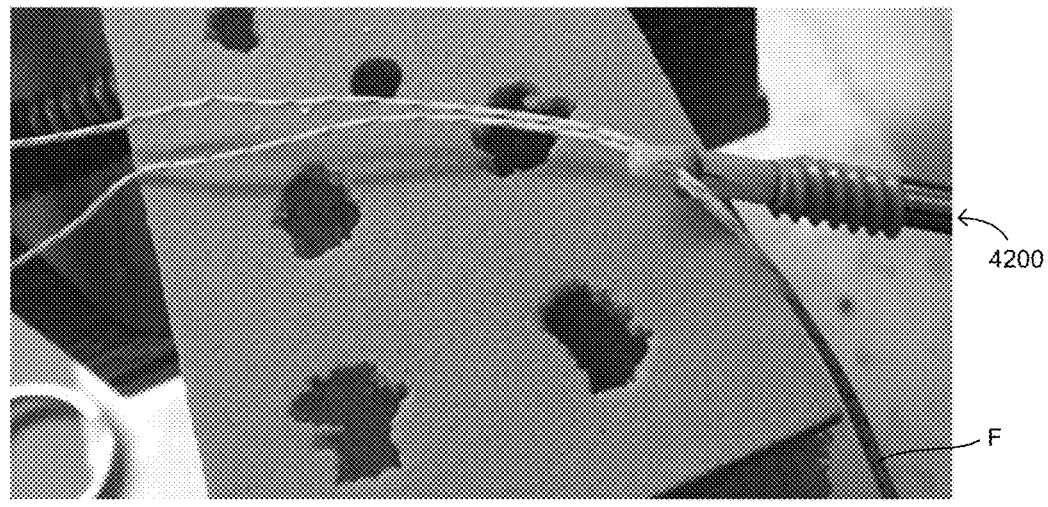
FIGS. 20A-20C illustrate one embodiment of a method of using an implant of the present disclosure, in particular the implant and inserter of FIGS. 18A-18E.
Figure 20B:
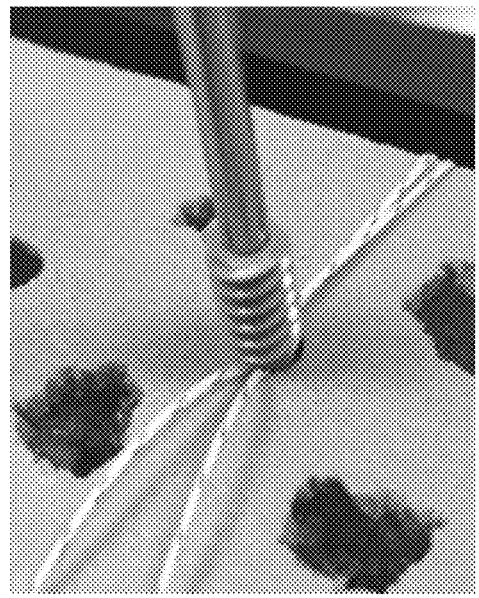
Figure 20C:
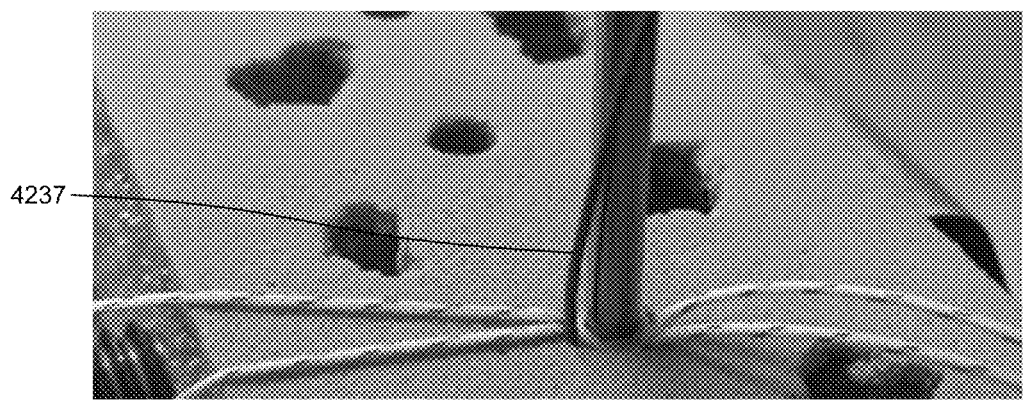

In one exemplary use, partially illustrated in FIGS. 20A-C, this implant 4200 may be inserted into a bonehole formed in bone, and initially, the implant can be inserted up to the beginning of the "fixation length," that is, up to the beginning of the fixation member 4250 such that that the eyelet 4220 and the associated filament F (positioned distal to suture 4237 and bores 4226), are within the bone. Then, the suture 4237 can be activated/released to allow translational movement of the filament to migrate into the cleat 4280. If the cleat on the proximal handle of the inserter 4260 is present, the suture 4237 can be released from the cleat to activate or release the suture to allow migration of the filament F into cleat 4280. Simultaneously with or after release of the suture 4237, the fixation member 4250 can be advanced via rotation thereof using the inserter 4260 to position the fixation member in the bone hole. The fixation member and eyelet may not have relative movement along a longitudinal axis of the inserter and implant, though the fixation member may have rotational movement relative to the eyelet (or the eyelet can rotate with the fixation member and inserter if desired). As to suture 4237, it may be pulled into the cleat area with the filament, or alternatively, the suture 4237 may be removed from the implant 4200 by, for example, pulling on one end of the suture 4237.

Further, in this example, the suture 4237 could have both of its limbs extend from the implant 4200 and up through the cannulation of the inserter (and fixation member) and to the proximal handle, or it could have only one limb go up into the cannulation. As to the latter configuration, as illustrated for example in FIGS. 18C-E and 20A-C, the opposite limb could be positioned outside the eyelet 4220 and could thus add additional compression fixation to the final construct by positioning itself between the fixation member 4250 and the bone.

In the still further example of both limbs of suture 4237 extending outside eyelet 4220 and fixation member 4250, the suture 4237 must be released and/or removed prior to initiation of insertion of fixation member 4250 into bone since, upon initiation, the suture 4237 would be trapped and thus prevent the filament from being able to migrate into cleat 4280.

As illustrated in FIG. 18A, the designated translational length may be substantially equal to or slightly less than the designated fixation length. A translational length slightly less than the fixation length may allow for some additional tensioning of the filament and may allow for deeper advancement of the filament into the cleat area to create additional frictional fixation on the suture.

Figure 19:
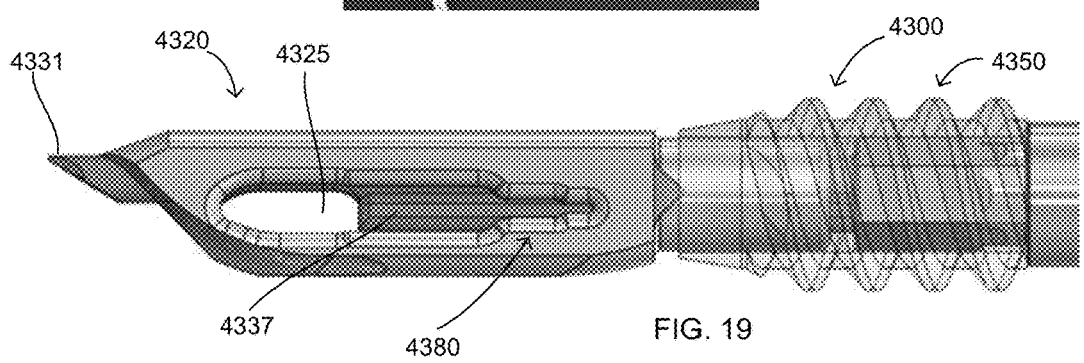
FIG. 19 illustrate yet another embodiment of the present disclosure, in particular, of an implant and an inserter.

In yet another embodiment of a combined implant, illustrated in FIG. 19 is implant 4300 including eyelet 4320 and fixation member 4350. Eyelet again includes cleat 4380 and awl 4330 includes a distal tip 4331 and a blocking feature 4337, as discussed above. In this embodiment, the implant 4300 and awl 4330 may be self-tapping or self-punching, similar to awl 30 and eyelet 20 above, such that drilling a bore hole or a pilot hole into the bone may be unnecessary, except perhaps in the hardest of bone. As in other such embodiments, a mallet or the like may be used to apply the distally-directed force to initiate punching through the cortical bone. Also as discussed above, the eyelet 4320 is cannulated to allow passage of the distal tip 4331 to protrude distal of the eyelet. Fixation member 4350 is also cannulated such that both the eyelet and the fixation member can be positioned on the awl together.

The fixation member 4350 may not have relative movement along a longitudinal axis of the awl 4330, though the fixation member may rotate relative to the eyelet 4320 (or the eyelet can rotate with the fixation member and inserter if desired). Alternatively, and as discussed in depth above, a small "gap" may exist between the proximal end of the eyelet and distal end of the fixation member. The gap may assist the distal portion of the instrument to deform a retention feature on the eyelet (similar to discussion above).

Figure 21A:
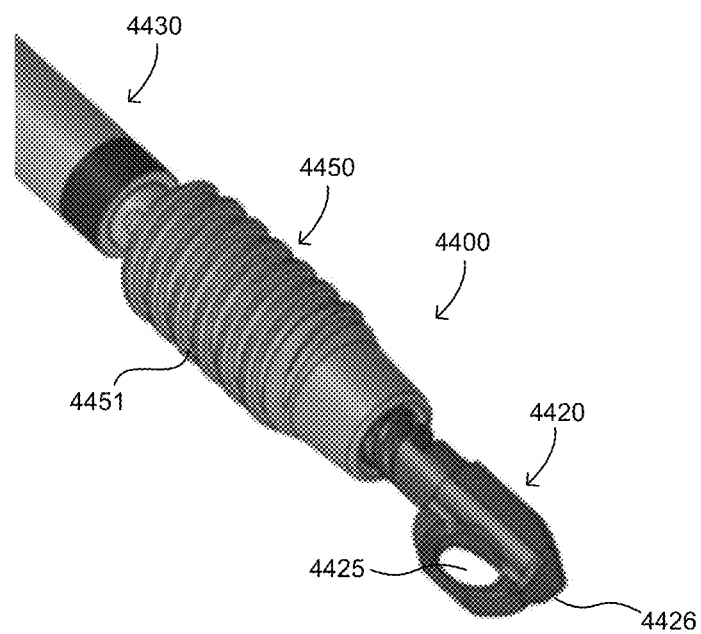
FIGS. 21A-21B illustrate still another embodiment of the present disclosure, in particular, of an implant and an inserter, with FIG. 21B illustrating a cross-section.
Figure 21B:
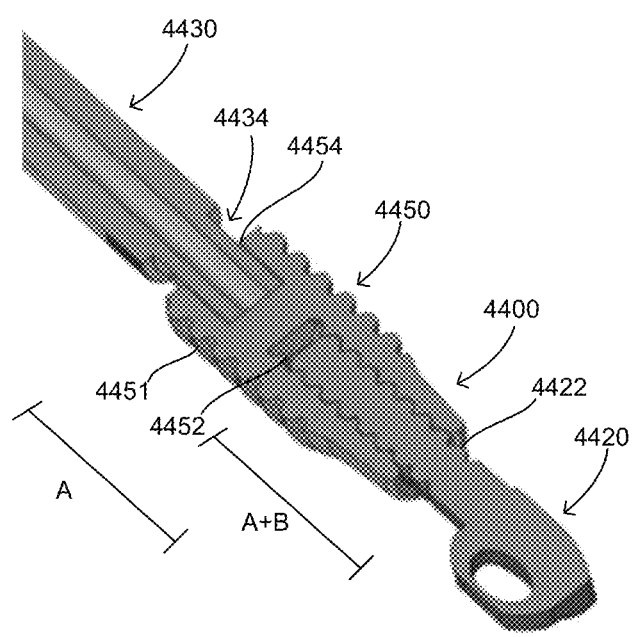

In still a further embodiment of a combined implant, illustrated in FIGS. 21A-B is implant 4400 including eyelet 4420 and fixation member 4450. Eyelet again includes throughbore 4425 and a distal end 4426, and may optionally include a cleat, a self-tapping distal end, or other features described herein as to other eyelet embodiments. Eyelet also includes in this embodiment an external thread 4422 along at least a portion of the eyelet, and as illustrated, the thread 4422 is along a proximal extension of the eyelet, extending proximally from the throughbore 4425. Fixation member 4450 includes an external thread 4451, similar to other embodiments discussed above, and also includes an internal thread 4452 which engages thread 4422 of eyelet 4420 and an instrument engagement feature 4454 which engages with a torque feature 4434 on inserter 4430.

Continuing with this embodiment, all threads 4451, 4452, 4422 have the same pitch, such that the same number of threads per length exist on all three threads. As such, implant 4400 is positioned on inserter 4430 and eyelet 4420 threads 4422 are partially threaded onto threads 4452, and in this position, a filament is passed through throughbore and the implant is ready for implantation into a bone. The positioning of threads 4422, 4452 in this position is such that the distance the threads can travel is substantially the same as the distance threads 4451 would travel into the bone. For example, if threads 4451 have a length A extending longitudinally along member 4450, threads 4422, 4452 would have a length A+B extending longitudinally along eyelet 4420 and within member 4450, respectively. In this example, the eyelet 4420 would be threaded onto member 4450 to a length B, such that both threads 4451 and threads 4422, 4452 can travel a length A during implantation.

Continuing with the illustrated example, with the eyelet 4420 and fixation member 4450 so positioned, the eyelet and engaged filament are positioned into a formed bonehole (unless eyelet 4420 includes a self-tapping distal end, in which case a mallet can be used to drive eyelet into the bone as described above). Once in position, the filament may be tensioned as desired to tension attached soft tissue. The inserter 4430 may then be used to rotate fixation member 4450, as described above, to engage threads 4451 with bone. Simultaneously, as threads 4451 engage bone, the eyelet 4420 may remain stationary relative to the bone (due to the tension of the filament, the offset throughbore 4425 contacting bone, or the like), and thus the threads 4422, 4452 also travel relative to one another. Since the threads 4451, 4422, 4452 all have substantially the same distance to travel, the threads 4422, 4452 should not bottom out before the completion of threading the fixation member 4450 into the bone, and thus the eyelet 4420 should not rotate relative to bone, which would minimize the risk of suture winding around the fixation member 4450. It should be noted that distances A and B in this example need not be exact, particularly since threads 4451 could, in some instances, travel deeper into the bone depending on the particular surgery and bone quality, and the eyelet 4420 could spin a small amount without sacrificing the quality of the repair. Thus, having all threads available to travel exactly a distance A is not required, and thus some deviations from these lengths is allowable.

Figure 22A:
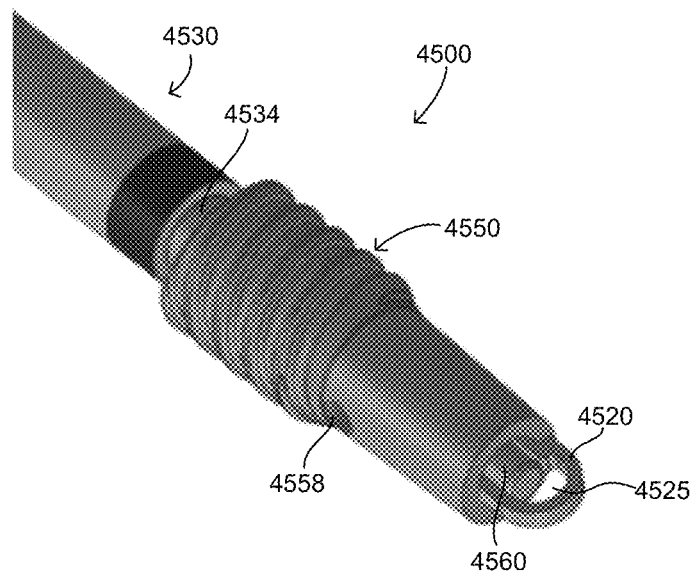
FIGS. 22A-22B illustrate yet a further embodiment of the present disclosure, in particular, of an implant and an inserter, with FIG. 22B illustrating a cross-section.
Figure 22B:
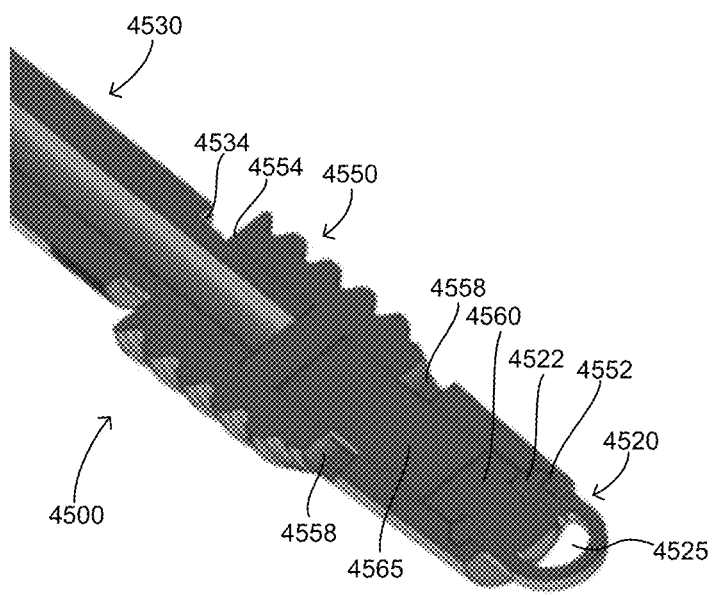

In another embodiment of a combined implant, illustrated in FIGS. 22A-B is implant 4500 including eyelet 4520 and fixation member 4550. In this embodiment, eyelet 4520 includes throughbore 4525 and tabs 4522 which reside within a groove 4552 within the distal portion of fixation member 4550. The tab-and-groove combination forms a swivel connection between the fixation member and eyelet such that, during implantation of the implant 4500, the fixation member is rotated (to engage the threads to the bone and secure the filament extending therebetween) but the eyelet remains stationary to prevent filament twisting. Fixation member also includes an instrument engagement feature 4554 which engages with a torque feature 4534 on inserter 4530. The fixation member 4550 also includes an internal cavity housing a volume of bioactive material 4565 and a piston 4560 adapted to translate along the longitudinal axis of the member 4550. The piston may apply pressure to the bioactive material 4565 to eventually expel the bioactive material from the fixation member 4550, such as through at least one transverse passage 4558, distally out of the member 4550 past the eyelet 4520, or the like. Piston 4560 can translate relative to the fixation member 4550 by any relative structure, such as matching threads or the like. For example, piston 4560 and eyelet 4520 may be rotatably fixed to one another, such that neither structure rotates during rotation of the fixation member 4550 during implantation of the implant 4500 into bone. Specifically, the tabs 4522 and groove 4552 arrangement allows the eyelet to remain stationary during rotation of the fixation member 4550, and piston 4560 may have a counter-rotation feature with the eyelet (e.g., channel and tab, or other non-circular shape). Thus, the matching threads between the piston and the fixation member, during such relative rotation, engage and cause the piston to move proximally, thereby applying pressure to expel the bioactive material from the fixation member. The bioactive material may be any known in the art to promote tissue growth, including for example hydroxyapatite, tricalcium phosphate, collagen-based additives, platelet-rich plasma, bioactive glass, or the like.

Depending on the amount of bioactive material 4565 included in the fixation member 4550, the overall length of the piston may be different from one implant 4500 to another. Further, such that there remains sufficient clearance within the throughbore 4525, the eyelet 4520 may also be lengthened in instances where the piston is particularly long.

In another alternative to implant 4500, the bioactive material 4565 compartment in the fixation member 4550 may not be present, and thus the piston 4560 also would not be present, and thus such an implant would include a fixation member and an eyelet having a swivel connection with the fixation member. Such an embodiment, as discussed herein, may include a cleat in the eyelet, in communication with the throughbore, as well as a cleat blocking feature to prevent premature cleating of the filament.

Any of the various features in the above-described embodiment may be utilized in any implant system, instrument and/or method as desired. For example, various implant and/or instrument systems may be self-tapping or not, and even self-tapping implants and instruments may require an initial pilot hole, for example in particularly hard bone. In another example of such alternatives, any of the above embodiments may additionally include bioactive material, as described above. In still another example, any of the disclosed eyelets or implant combinations can include a cleat, as well as a cleat blocking feature, which may provide additional fixation of the filament within the bonehole. Other such alternative combinations and configurations are also envisioned and are within the scope of the present disclosure.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An implant system for securing tissue to bone, comprising:
    a first fixation member releasably engaged to a first inserter,
        the first fixation member including a barb extending laterally from the proximal end in a first lateral direction relative to a longitudinal direction of the first fixation member and first inserter, a throughbore adapted to accept a filament therethrough and a cannulation extending from a proximal end of the first fixation member to a distal end of the first fixation member, the first inserter positioned through the cannulation and having a distal tip extending distally beyond the distal end of the first fixation member,
        the first inserter includes a shaft extending proximally from the distal tip, through the cannulation of the first fixation member, and to a handle, and a pocket having a distal surface tapering in the first lateral direction, a proximal surface tapering in a second lateral direction opposite the first lateral direction, and a flat surface in between the proximal and distal tapering surfaces oriented in the longitudinal direction, wherein at least a portion of the pocket coincides, in the longitudinal direction, with the barb of the first fixation member; and
    a second fixation member releasably engaged to a second inserter different from the first inserter.

2. The system of claim 1, wherein the cannulation and the throughbore are in communication with one another.

3. The system of claim 1, wherein the second fixation member includes at least one tissue engaging feature.

4. The system of claim 1, wherein the first fixation member includes a deformable portion and the first inserter includes a groove matingly received by the deformable portion, wherein the deformable portion is deformable between a mating position and a release position.

5. The system of claim 4, wherein the first inserter includes a shoulder positioned adjacent the proximal end of the first fixation member, the shoulder separated from the proximal end when the deformable portion is in the mating position and the shoulder abutting the proximal end when the deformable portion is in the release position.

6. The system of claim 5, wherein the first inserter is adapted to receive a driving force in the distal direction, wherein such driving force deforms the deformable portion from the mating position to the release position which provides for the proximal end of the eyelet to abut the shoulder.

7. The system of claim 1, wherein the distal tip of the first inserter and the distal end of the first fixation member combine into a distal surface adapted to form the bonehole.

8. The system of claim 1, wherein the first inserter and eyelet initiate a bonehole in the bone by the first inserter and eyelet moving along a path coaxial to a longitudinal axis of the bonehole as the distal end of the eyelet enters the bone, the first inserter and eyelet moving along a path lateral to the longitudinal axis of the bonehole as the barb and the distal surface of the pocket enter the bone, and first inserter and eyelet moving along the longitudinal axis of the bonehole after the proximal surface of the pocket enters the bone.

9. An implant system for securing tissue to bone, comprising:
    an eyelet releasably engaged to a first inserter, the eyelet having a throughbore adapted to accept a filament therethrough, a barb extending laterally from the proximal end in a first lateral direction relative to a longitudinal direction of the eyelet and first inserter, a deformable portion deformable between a mating position and a release position, and a cannulation extending from a proximal end of the eyelet to a distal end of the eyelet; and
    the first inserter positioned through the cannulation and having a distal tip extending distally beyond the distal end of the eyelet, the distal tip adapted to initiate a bonehole in the bone, a groove matingly received by the deformable portion when in the mating position, and a shaft extending proximally from the distal tip, through the cannulation of the eyelet, and to a handle, and a pocket having a distal surface tapering in the first lateral direction, a proximal surface tapering in a second lateral direction opposite the first lateral direction, and a flat surface in between the proximal and distal tapering surfaces, wherein at least a portion of the pocket coincides, in a longitudinal direction along the shaft, with the barb of the eyelet.

10. The system of claim 9, further comprising a fixation member releasably engaged to a second inserter different from the first inserter, the fixation member having a size capable of being positioned within the bonehole.

11. The system of claim 10, wherein the fixation member includes at least one tissue engaging feature.

12. The system of claim 9, wherein the cannulation and the throughbore are in communication with one another.

13. The system of claim 9, wherein the first inserter includes a shoulder positioned adjacent the proximal end of the eyelet, the shoulder separated from the proximal end when the deformable portion is in the mating position with the groove and the shoulder abutting the proximal end when the deformable portion is in the release position.

14. The system of claim 13, wherein the first inserter is adapted to receive a driving force in the distal direction, wherein such driving force deforms the deformable portion from the mating position to the release position which provides for the proximal end of the eyelet to abut the shoulder.

15. The system of claim 9, wherein the first inserter and eyelet initiate the bonehole in the bone by the first inserter and eyelet moving along a path coaxial to a longitudinal axis of the bonehole as the distal end of the eyelet enters the bone, the first inserter and eyelet moving along a path lateral to the longitudinal axis of the bonehole as the barb and the distal surface of the pocket enter the bone, and first inserter and eyelet moving along the longitudinal axis of the bonehole after the proximal surface of the pocket enters the bone.

16. An implant system for securing tissue to bone, comprising:
an eyelet releasably engaged to a first inserter, the eyelet including a barb extending laterally from the proximal end in a first lateral direction relative to a longitudinal direction of the eyelet and first inserter, a throughbore adapted to accept a filament therethrough, a cannulation extending from a proximal end of the eyelet to a distal end of the eyelet, and a deformable portion positioned in communication with the cannulation and deformable between a mating position and a release position; and
the first inserter positioned through the cannulation and having a distal tip extending distally beyond the distal end of the eyelet, the distal tip adapted to initiate a bonehole in the bone, a groove matingly received by the deformable portion when in the mating position, a shoulder positioned adjacent the proximal end of the eyelet, the shoulder separated from the proximal end when the deformable portion is in the mating position with the groove and the shoulder abutting the proximal end when the deformable portion is in the release position, and a shaft extending proximally from the distal tip, through the cannulation of the eyelet, and to a handle,
wherein the first inserter includes a pocket having a distal surface tapering in the first lateral direction, a proximal surface tapering in a second lateral direction opposite the first lateral direction, and a flat surface in between the proximal and distal tapering surfaces oriented in the longitudinal direction, wherein at least a portion of the pocket coincides, in a longitudinal direction along the shaft, with the barb of the eyelet.

17. The system of claim 16, further comprising a fixation member releasably engaged to a second inserter different from the first inserter, the fixation member having a size capable of being positioned within the bonehole.

18. The system of claim 17, wherein the fixation member includes at least one tissue engaging feature.

19. The system of claim 16, wherein the first inserter is adapted to receive a driving force in the distal direction, wherein such driving force deforms the deformable portion from the mating position to the release position which provides for the proximal end of the eyelet to abut the shoulder.

20. The system of claim 16, wherein the first inserter and eyelet initiate the bonehole in the bone by the first inserter and eyelet moving along a path coaxial to a longitudinal axis of the bonehole as the distal end of the eyelet enters the bone, the first inserter and eyelet moving along a path lateral to the longitudinal axis of the bonehole as the barb and the distal surface of the pocket enter the bone, and first inserter and eyelet moving along the longitudinal axis of the bonehole after the proximal surface of the pocket enters the bone.

* * * * *